(12) United States Patent
Oda et al.

(10) Patent No.: US 7,148,523 B2
(45) Date of Patent: *Dec. 12, 2006

(54) MOLECULAR RECTIFIER DEVICE

(75) Inventors: Masao Oda, Tokyo (JP); Hajime Matsumura, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/100,156

(22) Filed: Apr. 6, 2005

(65) Prior Publication Data

US 2005/0205895 A1    Sep. 22, 2005

Related U.S. Application Data

(63) Continuation of application No. 10/660,098, filed on Sep. 11, 2003, now Pat. No. 6,914,276.

(30) Foreign Application Priority Data

Sep. 11, 2002  (JP)  .............................. 2002-265924
Jul. 25, 2003  (JP)  .............................. 2003-279955

(51) Int. Cl.
   *H01L 23/58*   (2006.01)
(52) U.S. Cl. ............... 257/212; 257/414; 257/E51.023; 977/707
(58) Field of Classification Search ................ 257/212, 257/414, 658; 977/707, 791
See application file for complete search history.

(56) References Cited

U.S. PATENT DOCUMENTS 6,051,669 A * 4/2000 Attias et al. ................ 526/248
6,429,310 B1   8/2002 Kobuke et al.
6,914,276 B1 * 7/2005 Oda et al. ................... 257/212
2001/0027252 A1   10/2001 Kobuke et al.
2004/0202876 A1   10/2004 Kobuke et al.

FOREIGN PATENT DOCUMENTS

| JP | 2001/081091 A | 3/2001 |
| JP | P3256742 | 3/2001 |
| JP | 2001/213883 A | 8/2001 |
| JP | 2001/213945 A | 8/2001 |
| JP | 2001/253883 | 9/2001 |

OTHER PUBLICATIONS

Ogawa, Kazuya et al., "Large Third-Order Optical Nonlinearity of Self-Assembled Porphyrin Oligomers" J. Am. Chem. Soc., vol. 124, No. 1, 2002 pp. 22-23.

Ogawa, Kazuya et al., "Formation of a Giant Supramolecular Porphyrin Array by Self-Coordination" Agnew. Chem. Int. Ed., 2000, 39, No. 22, pp. 4070-4073.

* cited by examiner

*Primary Examiner*—Douglas W. Owens
*Assistant Examiner*—Thinh T. Nguyen
(74) *Attorney, Agent, or Firm*—Wolf, Greenfield & Sacks, P.C.

(57) ABSTRACT

A rectifier device, based on a novel operation principle completely different from that of conventional molecular electronic devices, is made by coupling two or more molecules or molecule arrays (11) at certain joints. By making use of the phenomenon that transfer of an excited state or exciton from one molecule or molecule array to another molecule or molecule array coupled thereto progresses asymmetrically due to spatial asymmetry at the joint, a rectifying function related to the transfer of the excited state of exciton is obtained. Additionally, by controlling the rectification property in addition to the rectification function, an ion sensor device or a switching device is made. A resistor device may be inserted in the rectifier device.

1 Claim, 24 Drawing Sheets

Fig. 3B
Fig. 3A
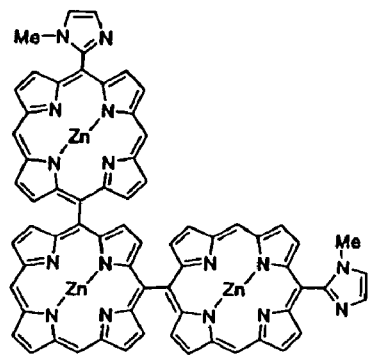
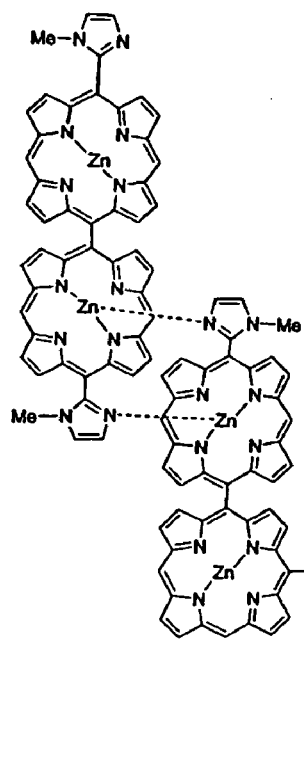
Fig. 3C
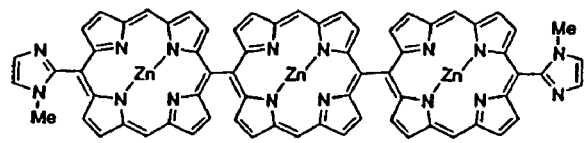

Fig. 16A  Fig. 16B

RECTIFICATION CONTROL BY Zn²⁺

MOLECULAR RECTIFIER DEVICE

CROSS REFERENCE TO RELATED APPLICATIONS

This application is a Continuation of application Ser. No. 10/660,098, filed on Sep. 11, 2003 now U.S. Pat. No. 6,914,276, entitled MOLECULAR DEVICE, MOLECULE ARRAY, RECTIFIER DEVICE, RECTIFYING METHOD, SENSOR DEVICE, SWITCHING DEVICE, CIRCUIT DEVICE, LOGICAL CIRCUIT DEVICE, OPERATIONAL DEVICE AND INFORMATION PROCESSING DEVICE which, in turn, claims priority to Japanese application No. JP2003-279955, filed Jul. 25, 2003 which, in turn, claims priority to Japanese application No. JP2002-265924 filed Sep. 11, 2002.

BACKGROUND OF THE INVENTION

1. Field of the Invention

This invention relates to a molecular device, molecule array, rectifier device, rectifying method, sensor device, switching device, circuit device, logical circuit device, operational device and information processing device.

2. Description of the Related Art

Molecular electronics for building devices having molecular electronic devices as their components to perform required functions have continuously gathered lots of interests since the proposal by A. Aviram, M. A. Ratner, et al. in 1974 (Non-patent Document 1: Chemical Physics Letter, vol. 29, 277(1974)) under anticipation to sophisticated and highly integrated devices based upon a concept completely different from conventional electronic devices (Non-patent Document 2: Y. Wada, M. Tsukada, M. Fujihira, K. Matsushige, T. Ogawa, M. Haga and S. Tanaka, Japanese Journal of Applied Physics, vol. 39, p. 3835 (2000)). Additionally, molecular electronics has recently been taken up as one of central issues of nanoscale science and technology.

Molecular electronic devices (or molecular nanoelectronics devices) heretofore proposed include a molecular switch composed of a molecule combining donors and acceptors; molecular conductor composed of linear-chain conjugate molecules, and so on (Non-patent Document 3: Y. Wada, H. Yamada, K. Matsushige, Applied Physics, vol. 70, p. 1396 (2001)).

Non-patent Document 4 (Y. Kobuke, "Supermolecular Porphyrin Functional Arrays", Material Integration, Vol. 14 No. 5, p. 59(2001)) and Non-patent Document 5 (K. Ogawa and Y. Kobuke, Angewandte Chemie International Edition, Vol. 39, p. 4070(2000)) report on meso-coupled imidazolyl porphyrin dimers. Non-patent Document 4 also comments on a photocurrent enhancing effect of a porphyrin array.

Patent Document 1 (JP2001-213945 A) discloses oligo(5, 15-diaryl-substituted Zn(II)-porphyrinylene) compounds extremely long up to 106 nm, for example, which compose monodisperse polymer rod of exact lengths and structures. Patent Document 2 discloses a novel mercapto-substituted imidazolyl porphyrin metal complex monomer and a polymer having the same as a repeating unit as well as their manufacturing methods. Patent Document 3 discloses a porphyrin dimer having imidazolyl porphyrin metal complex as a monomer. Patent Document 4 discloses poly (porphyrin) having an imidazolyl porphyrin metal complex as units.

Non-patent Document 6 (I. V. Rubtsov, Y. Kobuke, H. Miyaji, K. Yoshihara, "Energy Transfer in a Porphyrin Chelate Assembly", Chemical Physics Letters Vol. 308, 323 (1999)) reports that energy transfer between molecules takes place in approximately 10 picoseconds. Non-patent Document 7 (Homepage of Kobuke Laboratory, Internet, <URL: mswebs.aist-nara.ac.jp/LABs/kobuke/index-j.html> accessed on May 20, 2002) roughly explains application of porphyrin arrays to electronics.

Non-patent Document 8 (Imahori et al. "Photoactive three dimensional monolayers; Porphyrin-Alkanthiolate-stabilized gold cluster" (Imahori-jacs2001.pdf) and Non-patent Document 9 (H. Imahori and S. Fukuzumi, "Review on molecular solar cells", Kagaku Kogyo, vol. July 2001, p. 41) report about photoelectric conversion by combination of gold, thiol and $C_{60}$.

Non-patent Document 10 (N. Aratani, A. Osuka, Y. H. Kim, D. H. Jeong, D. Kim, "Extremely Long, Discrete meso-meso-Coupled Porphyrin Arrays", Angewandte Chemie International Edition, 39, No. 8, p. 1458(2000)) reports on synthesis and absorption spectrums of covalent porphyrin arrays. Used for synthesis is meso-meso-coupling reaction of 5,15-diaryl porphyrin (containing Zn as the central metal) promoted by $Ag^I$.

Non-patent Document 11 (N. Ohta, Y. Iwaki, T. Ito, I. Yamazaki, A. Osuka, "Photoinduced Charge Transfer along a meso-meso-linked Porphyrin Array", Journal of Physical Chemistry, B. Vol. 103, p. 11242(1999)) reports on measurement related to energy transfer (excitons) in a covalent porphyrin array. Measured here are properties of excitons parallel and perpendicular to longer molecular axes important for rectifier devices.

Non-patent Document 12 (A. Tsuda, H. Furuta, and A. Osuka, "Completely Fused Diporphyrins and Triporphyrin", Angewandte Chemie, International Edition, 39, No. 14, p. 2549(2000)) and Non-patent Document 13 (A. Ishida, "Observe behaviors of molecules from flows of electrons and energy", www.jst.go.jp/pr/announce/20000301/bessi3/kadai2.html) reports a flatly modified of a porphyrin polymer.

Non-patent Document 14 (K. Yamashita, "Conversion of Light Energy by Porphyrin", Hyomen, Vol. 21, No. 7, p. 406(1983)) describes changes in electron state of porphyrin molecules with their central metals in detail.

Non-patent Document 15 (K. Matsushige and K. Tanaka, "Molecular Nanotechnology", Kagaku Dojin, 1992) gives an explanation on design and synthesis of single-molecule devices in Chapter 13, an explanation on energy/electron transport devices by nanocoupled systems in Chapter 10, and an explanation on building of a molecular computer in Chapter 17.

Non-patent Document 16 (A. K. Burrell, D. L. Officer, P. G. Plieger and D. C. W. Reid, "Synthetic Routs to Multiporphyrin Arrays", Chemical Review, 101, p. 2751(2001) describes lots of examples of multiporphyrin arrays.

Non-patent Document 17 (Tetrahedron, Vol. 50, No. 39, p. 11427(1994)) describes a method of synthesizing meso-coupled imidazolyl porphyrin dimers.

Non-patent Document 18 (A. Ishida and T. Majima, "Surface Plasmon Excitation of Porphyrin self-assembly monolayers on an Au surface" Nanotechnology 10, p. 308 (1999)) reports on surface plasmon excitation of porphyrin.

Non-patent Document 19 (R. W. Wagner and J. S. Lindsey, "A Molecular Photonic Wire", J. Am. Chem. Soc. 1994, 116, 9759–9760.) reports on a method of modifying a terminal end of a porphyrin array and using light excitation thereby as an input.

Non-patent Document 20 ("Works of the group of Professor T. Yanagida in Osaka University", <URL: http://www.jst.go.jp/erato/project/ysu_P/syn/index.html> accessed on May 20, 2002) and Non-patent Document 21 (Catalogue of Products of Hamamatsu Photonics, <URL: http://www.hpk.co.jp/jpn/products/SYS/C8600J.htm> accessed on May 20, 2002) report on single-molecule imaging methods.

Non-patent Document 22 (Y. Kobuke and H. Miyaji, Journal of American Chemical Society 116, p. 4111(1994)) describes that fluorescent light from porphyrin has the wavelength of approximately 600±20 nm.

OBJECTS AND SUMMARY OF THE INVENTION

For practical use of molecular electronic devices, there are various problems including synthesis of molecular devices, confirmation of device functions, orientation control of molecular devices, fabrication of circuits by wiring between molecular devices or between molecular devices and external circuits, control of interactions among molecules caused by dense integration, reliability, operation speed, heat generation, resistance to environments, lifetime of devices, and so forth. With these problems, molecular electronics is still far from practical use. At the present moment, organic electronics that builds devices (such as organic EL (electroluminescence) devices) using macro organic materials (such as organic thin films) as their components are considered rather nearer to practical use than molecular electronics.

The present invention intends to overcome the present status of the conventional molecular electronics by a novel idea and to thereby reveal potential possibilities of molecular electronics. More specifically, this invention proposes a novel way of realization of nanoscale electronics transcending the conventional molecular electronics by looking to characteristic three principles in biological systems like photosynthesis, namely, energy transfer, exciton coupling and self assembly and positively introducing them.

That is, it is an object of the invention to provide a molecular device, molecule array, rectifier device, rectifying method, sensor device, switching device, circuit device, logical circuit device, operational device and information processing device based upon a novel principle of operation completely different from conventional molecular electronics devices.

The Inventors found a novel phenomenon through various researches. That is, in a system coupling two or more molecules or molecule arrays (especially, organic molecules or organic molecule arrays), or two or more kinds of such molecules or molecular arrays, at one or more certain joints, transfer of an excited state or exciton from one molecule or molecule array to another molecule or molecule array coupled thereto asymmetrically progresses because of spatial asymmetry at the their joint. Thus, the Inventors invented a device having a rectifying function related to the transfer of the excited state or exciton as a device using the novel phenomenon, and further invented various devices such as switching devices, sensor devices and logical circuit devices, making use of the rectifying function or the function of controlling the rectifying property.

In order to achieve the aforementioned object, according to the first aspect of the invention, there is provided a molecular device having a rectifying function to cause asymmetrical progress of transfer of an excited state or exciton.

The excited state or the exciton may be formed or generated by stimulating the device from outside. Alternatively, an excited state or exciton generated outside may be injected. Alternatively, these both may be combined. Light such as visible light is typically used as the external stimulation.

This molecular device generally includes at least two (either of one kind or of two or more kinds) molecules or molecule arrays (especially, organic molecules or organic molecule arrays) as its components. The number, kind, placement and other features of these molecules or molecule arrays are determined depending upon the intended function of the molecular device. More specifically, at least two molecules or molecule arrays may be those that have straight or linear shapes and can be excited directly by light or can make an excited state by transfer of excitation energy from an adjacent molecule or molecule array, for example. The straight or linear molecule or molecular array may be a conjugate polymer in form of a linear chain, a non-conjugate polymer in form of a linear chain, or a linear molecule aggregate composed of the same or different kinds of molecules represented by an aggregate of cyanine family dyes.

Alternatively, at least two molecules or molecule arrays may be those that have cyclic or elliptic shapes and can be excited directly by light or can make an excited state by transfer of excitation energy from an adjacent molecule or molecule array, for example. The cyclic or elliptic molecule or molecule array may be a cyclic conjugate polymer, a cyclic non-conjugate polymer, or a cyclic molecule aggregate composed of the same or different kinds of molecules represented by light-collecting structures of photosynthesis. There are porphyrin molecules and phthalocyanine molecules as examples of molecules or molecule arrays.

In a typical structure of the molecular device, one molecule or molecule array physically or chemically couples with at least one other molecule or molecule array by conjugated bond, non-conjugated covalent bond (saturated bond), charge transfer bond, ionic bond, hydrogen bond, stacking by interaction of n electrons, Van der Waals force or their intermediate force. Then, typically, a rectifying function is brought about by using the phenomenon that transfer of the excited state or exciton progresses asymmetrically or irreversibly between at least two molecules or molecule arrays that are physically or chemically bonded. Most typically, as a result of these two or more molecules or molecule arrays under physical or chemical bond being non-parallel at their joint, transfer of the excited state or exciton asymmetrically progresses. In other words, transfer of the excited state or exciton progresses asymmetrically in the molecular device because at least two molecules or molecule arrays bond together to form a joint and the joint exhibits spatial asymmetry at the site of coupling.

In case at least two molecules or molecule arrays (especially, organic molecules or organic molecule arrays) are used in the molecular device as its components, they may be coupled via a resistor device inserted between them. The resistor device may be a molecule or molecule array, especially an organic molecule or organic molecule array, (normally different from the molecules or molecule arrays composing the molecular device), and they make covalent bond with the molecules or molecule arrays composing the molecular device. The molecule or molecule array used as the resistor device may be one that changes in structure by irradiation of electromagnetic waves (light-responsive molecules, etc.) or one that changes in structure with temperature (heat-responsive molecules, etc.), depending on the necessity. Although the molecule will be selected depending upon the particular purpose, its examples are benzene, azobenzene, alkyne, cycloalkane (like cyclohexane), bi-cyclo[2,2,2]alkane (like bi-cyclo[2,2,2]hexane), and others. In some cases, various bonds like a peptide bond or various groups like an ago group may be also used as the resistor device. Distance between molecules or molecule arrays coupled at opposite ends of the resistor device can be changed, for example, by changing the size of the molecule or molecule array used as the resistor device as well as the relative angle in the coupling direction between the molecules or molecule arrays that compose the molecular device and couple to the opposite ends of the molecule or molecule array as the resistor device. Since the transition dipole interaction between two transition dipole moments is inversely proportional to the sixth power of the distance between them, it is possible to control the transition dipole interaction and thereby control transfer of the excited state or exciton by controlling the distance between the molecules or molecule arrays.

In order to input excited state or exciton into the molecular device from outside, at least one input terminal is typically formed in at least one molecule or molecule array composing the molecular device. Number and position of the input terminal is determined depending upon the intended function of the molecular device. Examples of the input method are the method of inducing surface plasmon excitation by light at the input terminal and thereby inputting an excited state or exciton, the method of modifying a terminal end of a molecule or molecule array with a dye molecule having predetermined molecular orbital energy and using it as the input terminal so as to input an excited state or exciton by photo excitation there.

According to the second aspect of the invention, there is provided a molecule array having a rectifying function to cause asymmetrical progress of transfer of an excited state or exciton.

According to the third aspect of the invention, there is provided a rectifier device having a rectifying function to cause asymmetric progress of transfer of an excited state or exciton.

According to the fourth aspect of the invention, there is provided a rectifying method characterized in causing asymmetric progress of transfer of an excited state or exciton.

According to the fifth aspect of he invention, there is provided a sensor device having a rectifying function to cause asymmetrical progress of transfer of an excited state or exciton and a function to control the rectifying property.

The sensor device generally includes at least two molecules or molecule arrays as its components. Typically, at least one of these molecules or molecule arrays has an ion recognizing function, and the device carries out ion sensing by using the phenomenon that the rectifying property changes depending upon whether there are any ions that adhere to the site having the ion recognizing function.

According to the sixth aspect of the invention, there is provided a switching device having a rectifying function to cause asymmetric progress of transfer of an excited state or exciton and a function to control the rectifying property.

The switching device generally includes at least two molecules or molecule arrays as its components. Typically, at least one of these molecules or molecule arrays has an ion recognizing function, and the device performs ion sensing by using the phenomenon that the rectifying property changes depending upon whether there are any ions that adhere to the site having the ion recognizing function.

According to the seventh aspect of the invention, there is provided a circuit device comprising a switching device as a component thereof, the switching device having a rectifying function to cause asymmetric progress of transfer of an excited state or exciton and a function to control the rectifying property.

The circuit device is usable for various purposes, and includes one or more switching devices depending upon the intended use or function thereof. The circuit device may be a logical circuit device, for example.

According to the eighth aspect of the invention, there is provided a logical circuit device comprising a switching device as a component thereof, the switching device having a rectifying function to cause asymmetric progress of transfer of an excited state or exciton and a function to control the rectifying property.

The logical circuit device includes one or more switching devices depending upon the intended function thereof.

According to the ninth aspect of the invention, there is provided an operational device comprising a switching device as a component thereof, the switching device having a rectifying function to cause asymmetric progress of transfer of an excited state or exciton and a function to control the rectifying property.

The operational device includes one or more switching devices depending upon the intended operational function thereof.

According to the tenth aspect of the invention, there is provided an information processing device comprising a switching device as a component thereof, the switching device having a rectifying function to cause asymmetrical progress of transfer of an excited state or exciton and a function to control the rectifying property.

The information processing device includes one or more switching devices depending upon the intended information processing function thereof.

Explanation given above with reference to the first aspect of the invention is also applicable to the second to tenth aspects of the invention within the extent not contravening their natures.

Similarly, explanation given above with reference to the sixth aspect of the invention is also applicable to the seventh to tenth aspects of the invention within the extent not contravening their natures.

The invention having the above-summarized features can obtain a rectifying function to cause asymmetrical progress of transfer of an excited state or exciton by using molecules or molecule arrays as its base.

The above and other objects and features of the present invention will become apparent from the following detailed description and the appended claims with reference to the accompanying drawings.

BRIEF DESCRIPTION OF THE DRAWINGS

FIGS. 3A through 3C are schematic diagrams for explaining a concrete structure of the rectifier device according to the first embodiment of the invention;

DETAILED DESCRIPTION OF THE PREFERRED EMBODIMENTS

Figure 1A:
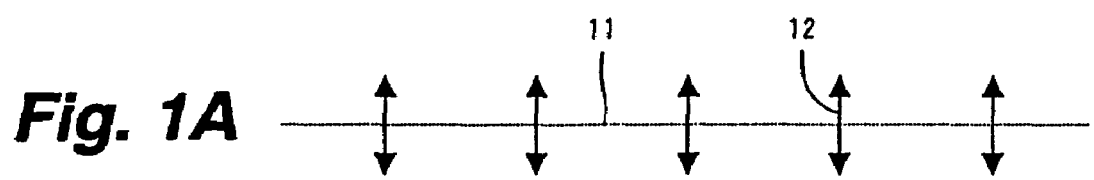
FIGS. 1A through 1C are schematic diagrams showing a rectifier device according to the first embodiment of the invention.

Embodiments of the invention will now be explained below with reference to the drawings. In all drawings showing embodiments of the invention, common or corresponding elements are labeled with common reference numerals.

Figure 1B:
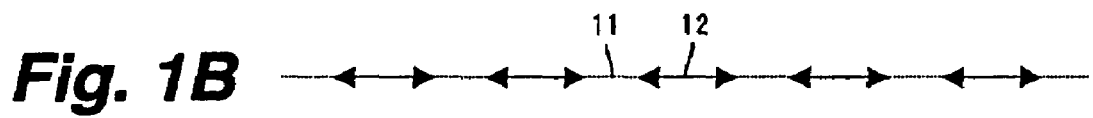
Figure 1C:
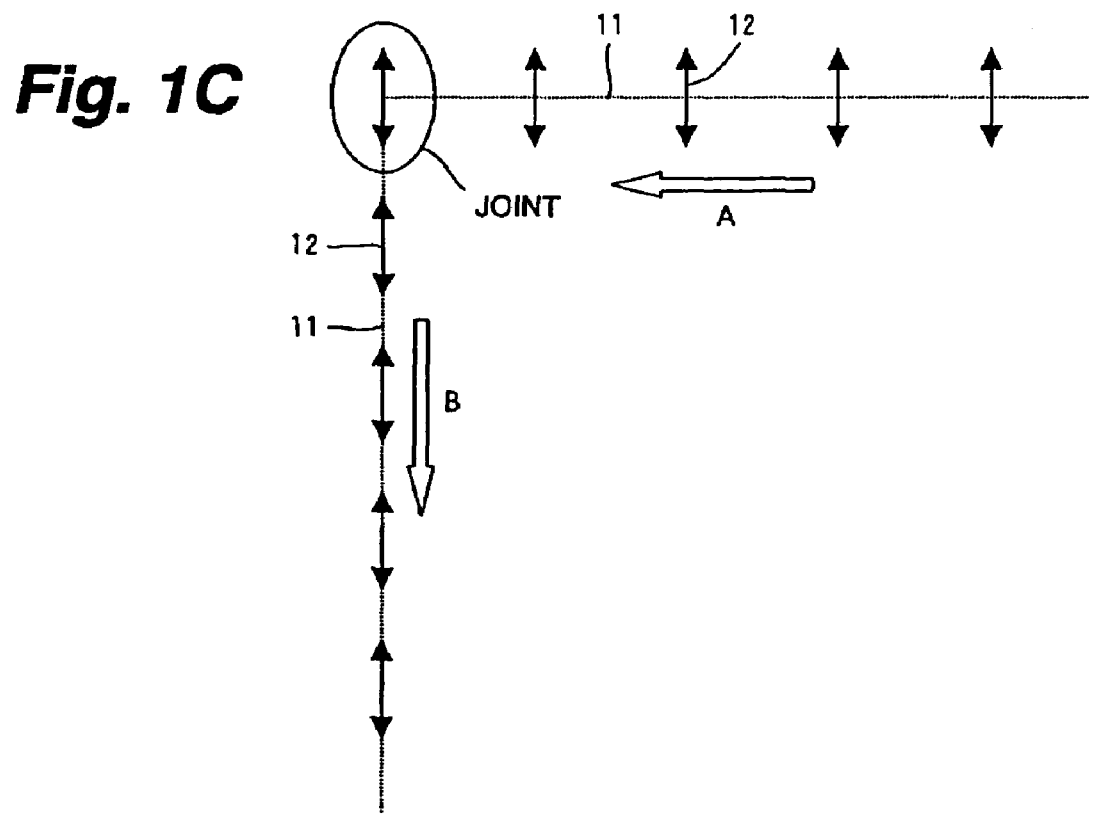

FIGS. 1A through 1C show the first embodiment of the invention. Here is explained a rectifying effect appearing when two straight or linear molecules or molecule arrays are bonded together at a right angle.

With reference to FIGS. 1A and 1B, a review is made on excitons 12 composed of one more electron transitions having transition dipole moments perpendicular (FIG. 1A) and parallel (FIG. 1B) to the longer axes of straight or linear molecules or molecule arrays (double-headed arrows show directions of polarization). Energy levels of the excitons 12 of these two states are determined by the magnitude and placement of interaction between the transition dipole moments.

FIG. 1C shows a structure of a rectifier device that is obtained by coupling two identical straight or linear molecules or molecule arrays 11 at their terminal ends at a right angle. In this case, when the exciton 12 polarized perpendicularly to the longer axis of the molecule or molecule array 11 (FIG. 1A) has a higher energy level, the exciton 12 transfers in the arrow A and B directions with a higher probability. That is, asymmetry occurs in transfer of the exciton 12, and a rectification effect is obtained concerning the transfer of the exciton 12.

In case the exciton 12 polarized in parallel to the longer axis of the molecule or molecule array 11 (FIG. 1B) has a higher energy level, the exciton 12 transfers in directions opposite from the arrows A and B with a higher possibility. Here again, asymmetry occurs in transfer of the exciton 12, and a rectification effect is obtained concerning the transfer of the exciton 12.

The above-explained asymmetry of the transfer of the exciton 12, i.e. the rectification effect concerning the transfer of the exciton 12, are brought about by spatial asymmetry of the joint at the coupling site of two straight or linear molecules or molecule arrays 11.

Next explained is a concrete structure of the rectifier device.

Figure 2A:
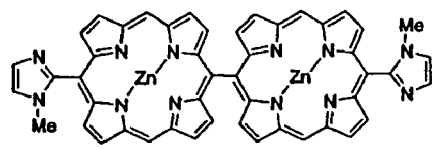
FIGS. 2A through 2D are schematic diagrams for explaining a concrete structure of the rectifier device according to the first embodiment of the invention.

FIG. 2A shows a meso-coupled imidazolyl porphyrin dimer (Non-patent Document 4). This meso-coupled imidazolyl porphyrin dimer composes the linear molecule array by complementary coordinate bonding as shown in FIG. 2B (Non-patent Document 5).

Figure 2B:
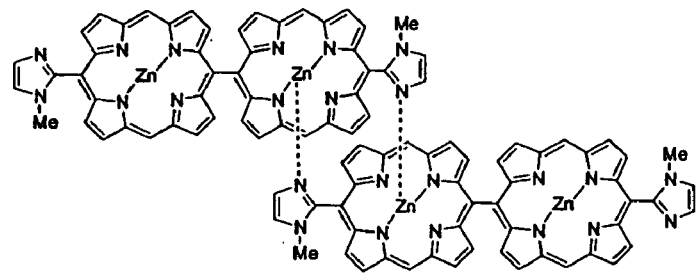
Figure 2C:
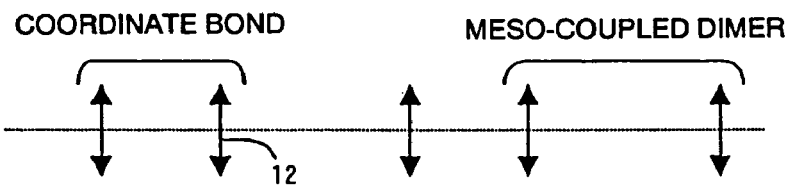
Figure 2D:
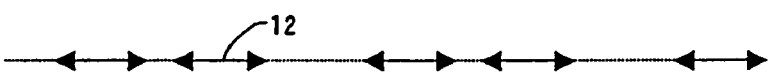

In the linear molecule array shown in FIG. 2B, there are two kinds of excitons (shown in FIGS. 2C and 2D, respectively) composed of electron transitions having transition dipole moments perpendicular and parallel to the longer axes of the molecules, and the exciton polarized in parallel to the longer axis of the molecule (exciton in FIG. 2D) have a higher energy level.

FIG. 3A shows a meso-coupled nonlinear imidazolyl porphyrin trimer. A linear molecule array can be made by coordinate bonding in two directions perpendicular to each other from the meso-coupled nonlinear imidazolyl porphyrin trimer as the starting point as shown in FIG. 3B to form the rectifier device as shown in FIG. 1C. In this case, the building block forming the linear portion may be composed of either the meso-coupled linear imidazolyl porphyrin trimer shown in FIG. 3C or the meso-coupled linear imidazolyl porphyrin dimer of FIG. 2A. In the example of FIG. 3B, the latter meso-coupled linear imidazolyl porphyrin dimer is used.

There are lots of researches on porphyrin system substances and studies on their applications (Patent Document 1 through 4 and Non-patent Documents 4 through 22).

Non-patent Document 14 describes details of changes of electron states of porphyrin molecules with central metals used. With reference to first reduction potentials (E(P/P$^-$)) in Table 4 (p. 414) in conjunction with FIG. 11 (p. 412) of this document, Pd is the only central metal that has E(P/P$^-$) smaller than that of H$_2$. In case that porphyrin with any other central metal is used as the crossing point of an exciton rectifier device, then the excitons will be trapped at their positions, and this leads to sensing or switching by ions.

Figure 4:
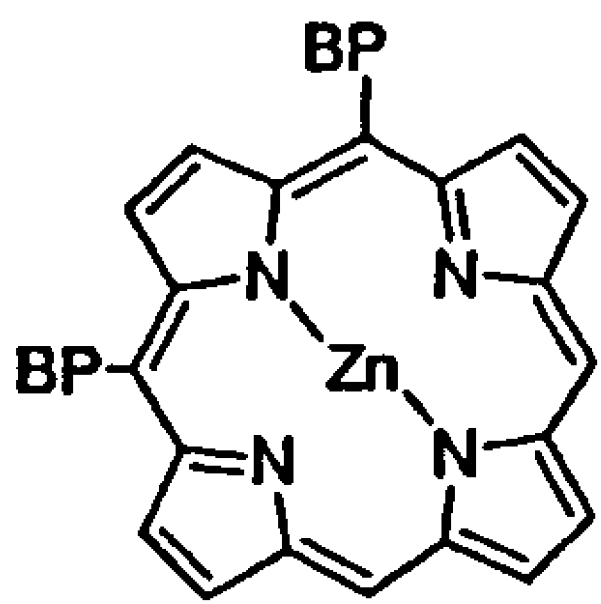
FIG. 4 is a schematic diagram for explaining a concrete structure of the rectifier device according to the first embodiment of the invention.

For synthesis of molecules forming the basic structure of the rectifier device, Scheme 17, Scheme 19 and Scheme 21 of Non-patent Document 16 are used, for example. Especially upon synthesizing the crossing point of the rectifier device, in the process of reaction forming the molecule 54 from the molecule 53 in Scheme 21, the molecule shown in FIG. 4 similar to the molecule 53 is mixed by a half amount of the molecule 53 in addition to the molecule 53. Thereby, a trimer bent at a right angle can be made. In FIG. 4, BP is an allyl group (including a donor- or acceptor-natured substituent) or an alkyl group.

Figure 5:
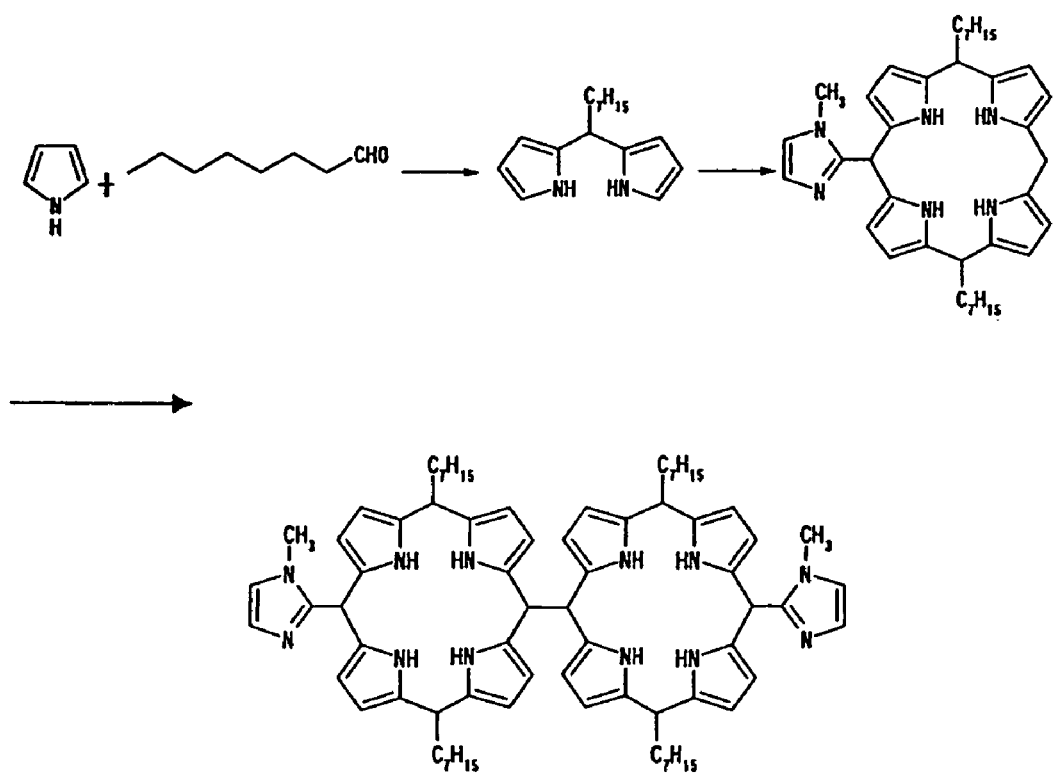
FIG. 5 is a schematic diagram for explaining an example of synthesis of a porphyrin family substance to be used for fabrication of the rectifier device according to the first embodiment of the invention.
Figure 6:
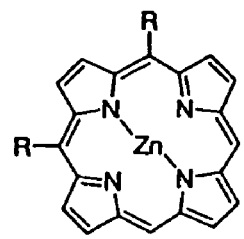
FIG. 6 is a schematic diagram for explaining an example of synthesis of a porphyrin family substance to be used for fabrication of the rectifier device according to the first embodiment of the invention.

The meso-coupled imidazolyl porphyrin dimer as the basic structural component of the coordinate-bonded molecule array can be synthesized by the reaction shown in FIG. 5, for example (Non-patent Document 17). If the final reaction (formation of the dimer) of this synthesis is modified by adding the molecule shown in FIG. 6 by 0.5 times to invite further reaction, then the bent meso-coupled nonlinear imidazolyl porphyrin trimer as shown in FIG. 3A can be synthesized. The substituent in FIG. 5 need not be C$_7$H$_{15}$, but alkylamino group (the alkyl is branched alkyl or straight-chain alkyl), nitro group, cyano group, and so forth, are also usable.

Figure 7:
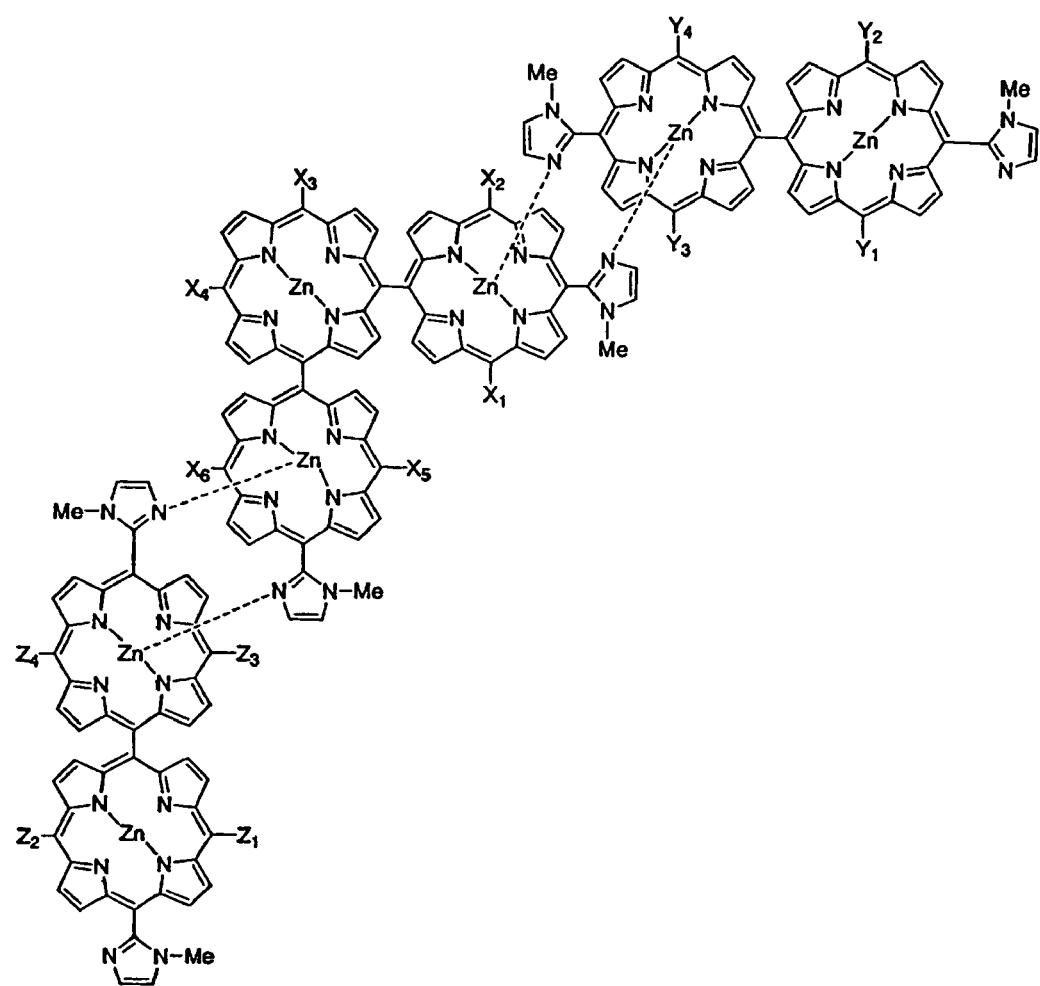
FIG. 7 is a schematic diagram for explaining a concrete structure of the rectifier device according to the first embodiment of the invention.

Here is explained an example introducing substituents into a coordinate-bonded porphyrin array (Kobuke type) with reference to FIG. 7.

Substituents Xai, Xbi, Ya(1, 2, 3, . . . , n, . . . , N), Yb(1, 2, 3, . . . , n, . . . , N) Za(1, 2, 3, . . . , n, . . . , N) and Zb(1, 2, 3, . . . , n, . . . , N) include the following donor- or acceptor-natured substituents.

Donor-Natured Substituents

—NR$_2$ and R are branched or linear substituents (alkyl group and alkoxy group) made of C, H and C.

Acceptor-Natured Substituents

There are —CN (cyano group), NO$_2$ (nitro group) and SO$_3$H (sulpho group).

Figure 8:
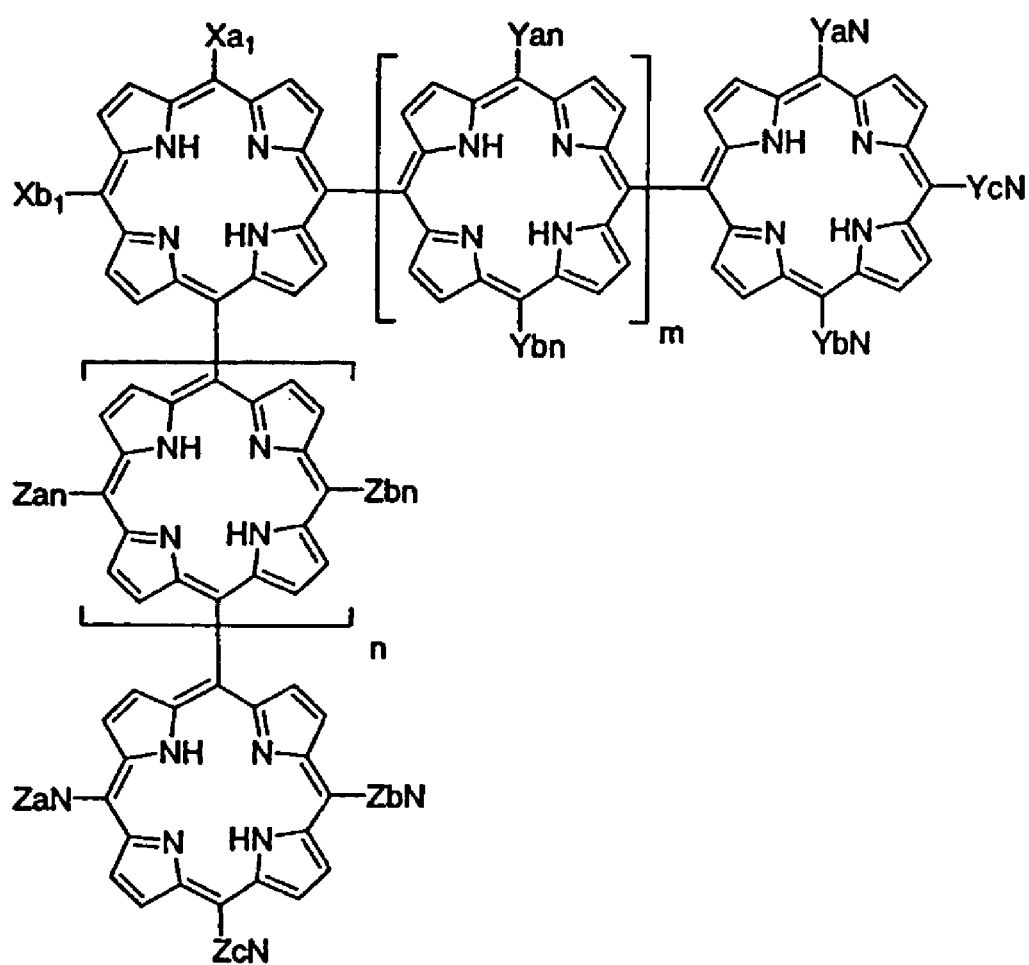
FIG. 8 is a schematic diagram for explaining a concrete structure of the rectifier device according to the first embodiment of the invention.

Next explained is an example introducing substituents into a covalent porphyrin array (Osuga type) and including no central metal (FIG. 8).

The following benzene ring (allyl group) having a donor- or acceptor-natured substituent is introduced as substituents Xai, Xbi, Ya(1, 2, 3, . . . , n, . . . , N), Yb(1, 2, 3, . . . , n, . . . , N), Za(1, 2, 3, . . . , n, . . . , N) and Zb(1, 2, 3, . . . , n, . . . , N).

Allyl Groups Having Donor-Natured Substituents

—NR$_2$ and R are branched or linear substituents (alkyl group and alkoxy group) made of C, H and C.

Allyl Groups Having Acceptor-Natured Substituents

There are —CN (cyano group), NO$_2$ (nitro group) and SO$_3$H (sulpho group).

Figure 9:
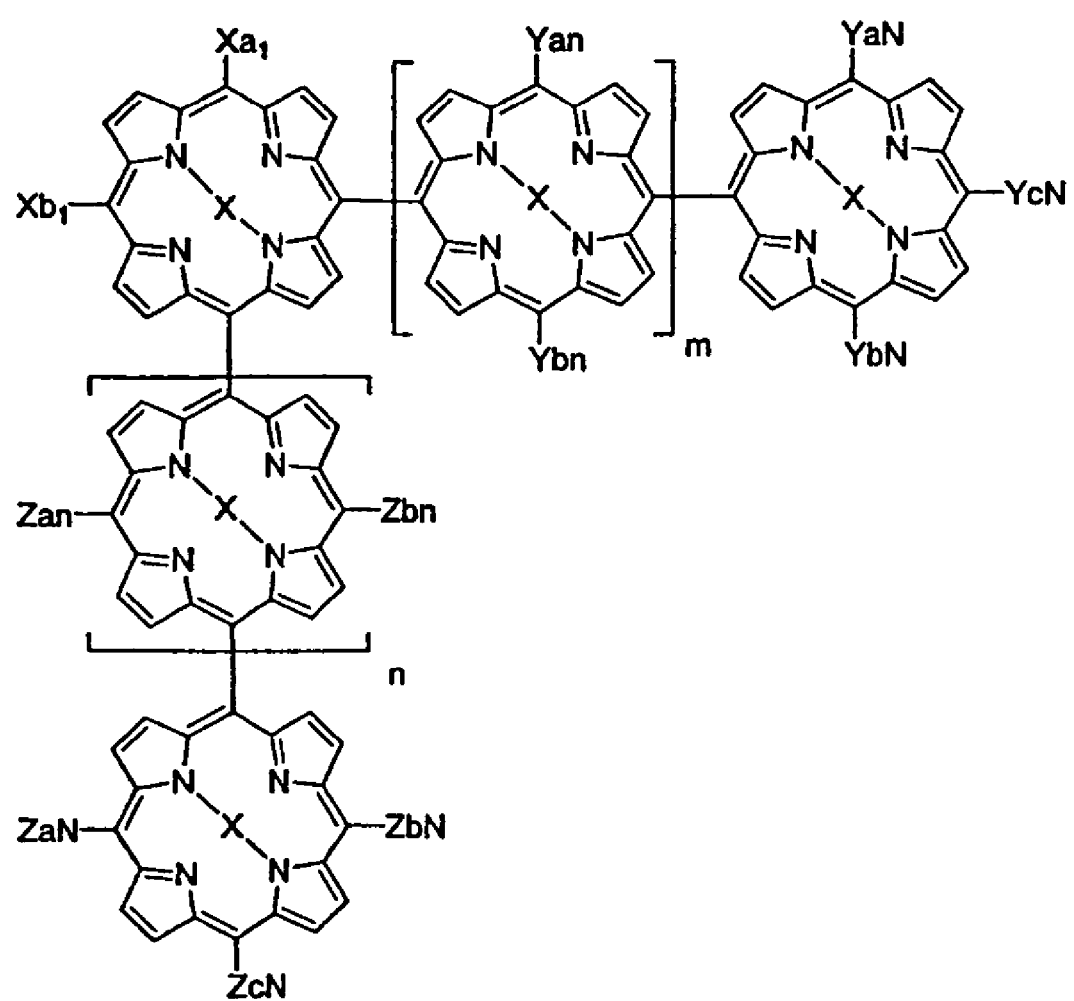
FIG. 9 is a schematic diagram for explaining a concrete structure of the rectifier device according to the first embodiment of the invention.

Next explained is an example introducing substituents into a covalent porphyrin array (Osuga type) and including a central metal (FIG. 9).

The following benzene rings (allyl groups) having donor- or acceptor-natured substituents are introduced as substituents Xai, Xbi, Ya(1, 2, 3, . . . , n, . . . , N), Yb(1, 2, 3, . . . , n, . . . , N), Za(1, 2, 3, . . . , n, . . . , N) and Zb(1, 2, 3, . . . , n, . . . , N).

Allyl Groups Having Donor-Natured Substituents

—NR$_2$ and R are branched or linear substituents (alkyl group and alkoxy group) made of C, H and C.

Allyl Groups Having Acceptor-Natured Substituents

There are —CN (cyano group), NO$_2$ (nitro group) and SO$_3$H (sulpho group).

Excited states or excitons can be input to the rectifier device in the following manner, for example.

Figure 10:
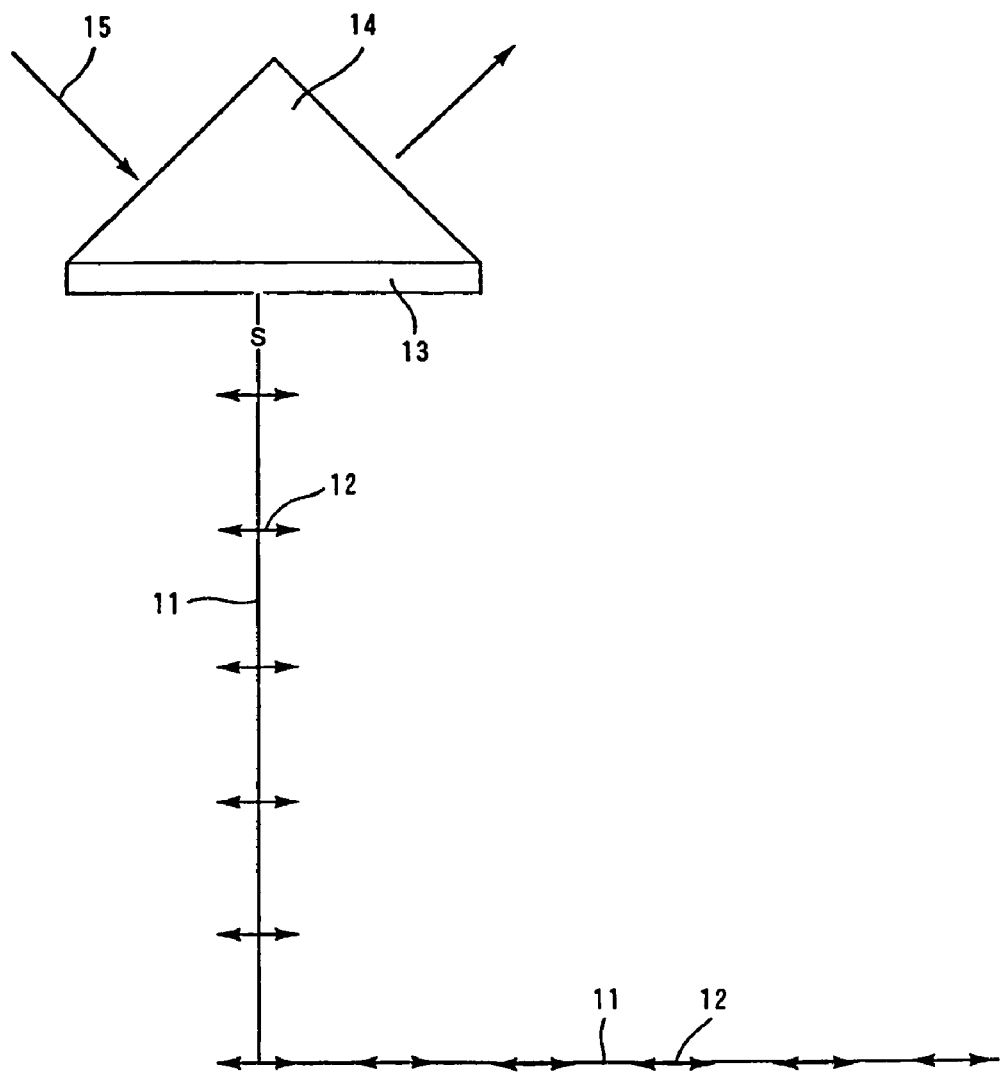
FIG. 10 is a schematic diagram for explaining an exemplary input terminal of the rectifier device according to the first embodiment of the invention.
Figure 11:
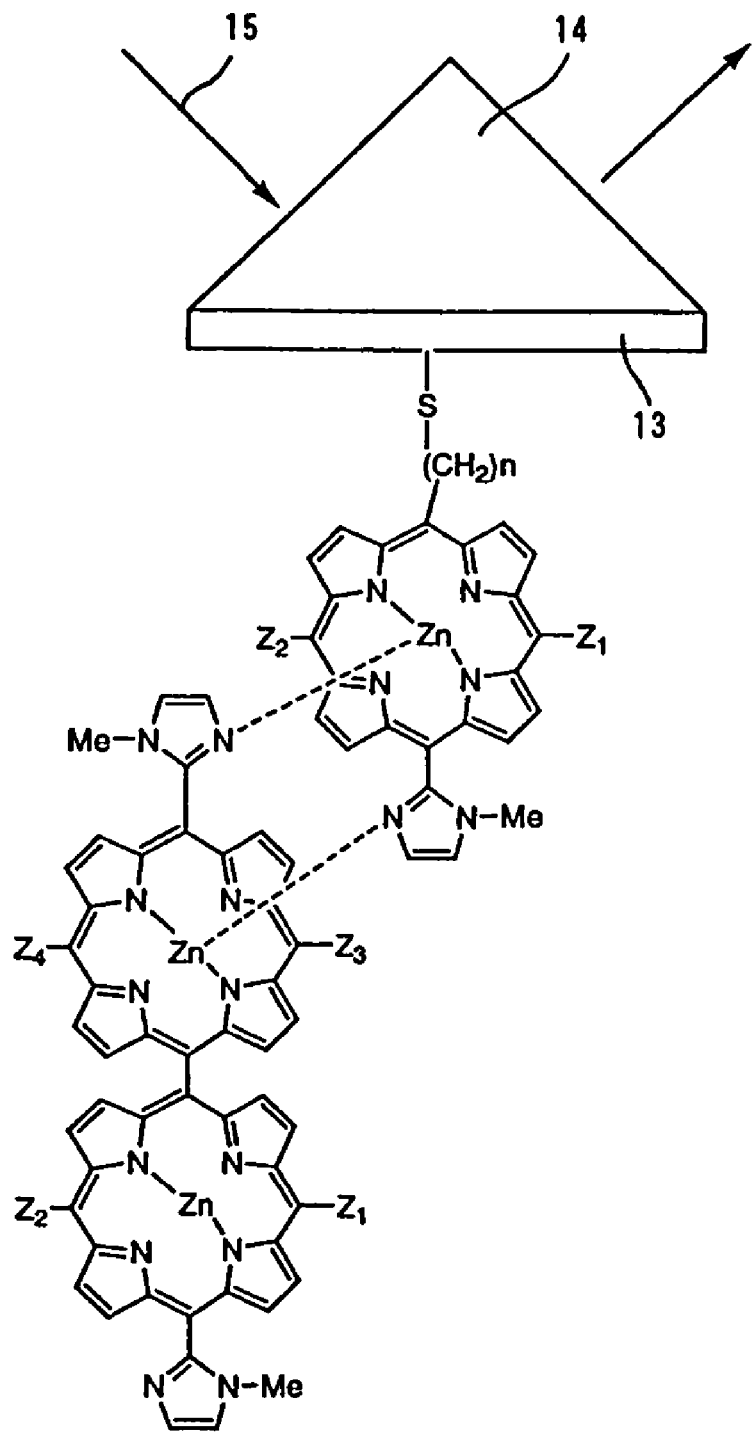
FIG. 11 is a schematic diagram for explaining an exemplary input terminal of the rectifier device according to the first embodiment of the invention.

FIG. 10 shows this example. As shown in FIG. 10, a terminal end of molecules or molecule arrays 11 is connected to one of surfaces of a metal film 13 made of Au, Ag, Pt, or the like, by using thiol. The other surface of the metal film 13 is kept in close contact with a rectangular prism 14. A concrete structure of the molecules or molecule arrays 11 is shown in FIG. 11.

When light 15 is introduced from outside onto one of two rectangularly crossing surfaces of the rectangular prism 14 at the input terminal having the above-mentioned structure, surface plasmon is excited in the metal film 13, and an exciton 12 is thereby generated at the terminal end of the molecules or molecule arrays 11.

Surface plasmon excitation can be brought about not only by light but also by charged particles such as electrons.

Surface plasmon excitation of porphyrin is reported in Non-patent Document 18.

One of other methods of inputting excited states of excitons other than the aforementioned surface plasmon excitation modifies a terminal end of molecules or molecule arrays 11, such as porphyrin arrays for example, with a dye molecule (boron-dipyrromethene) having adequate molecular orbit energy and uses light excitation there as the input (Non-patent Document 19).

One of methods for outputting from the rectifier device modifies the site for extraction of a signal from the molecules or molecule arrays 11 composing the rectifier device with an adequate molecule emitting fluorescent light. A concrete process of this method is as follows. A terminal end of the molecule or molecule array 11 forming the rectifier device is modified with a fluorescent dye. An excited state or exciton introduced to the molecules or molecule arrays 11 finally reaches the fluorescent dye, and the fluorescent dye emits fluorescent light. Then, by using a single-molecule imaging method (shown in Non-patent Documents 20, 21, for example), fluorescent light from a single fluorescent dye is imaged by a CCD camera. With regard to concrete examples of fluorescent dyes for modifying the terminal end of the molecules or molecule arrays 11, in case the molecules or molecule arrays 11 are porphyrin arrays, for example, the use of one from the porphyrin arrays themselves will be the easiest way. As to fluorescent light from porphyrin, Non-patent Document 22 explains as having a wavelength around 600±20 nm. In case of modifying the terminal end of the molecules or molecule arrays 11 with a fluorescent dye other than porphyrin, it will be necessary that the dye is a molecule having a lowest unoccupied molecular orbital (LUMO) causing generation of energy from porphyrin. C$_{60}$, although not emitting fluorescent light, is a molecule permitting energy transfer from porphyrin.

Figure 12:
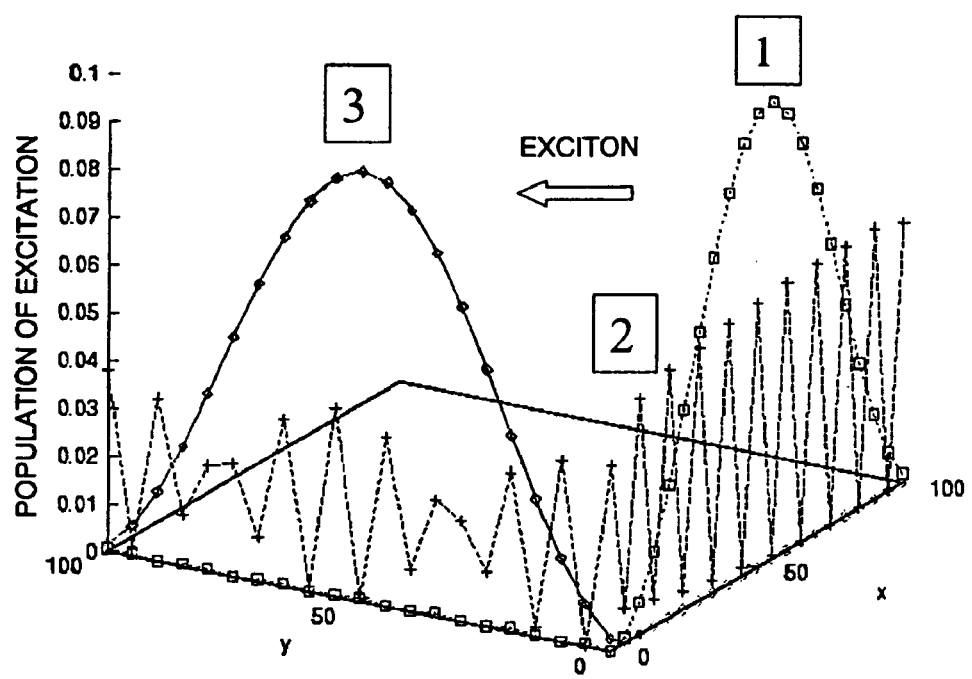
FIG. 12 is a schematic diagram showing a result of simulation carried out with the rectifier device according to the first embodiment of the invention.
Figure 13:
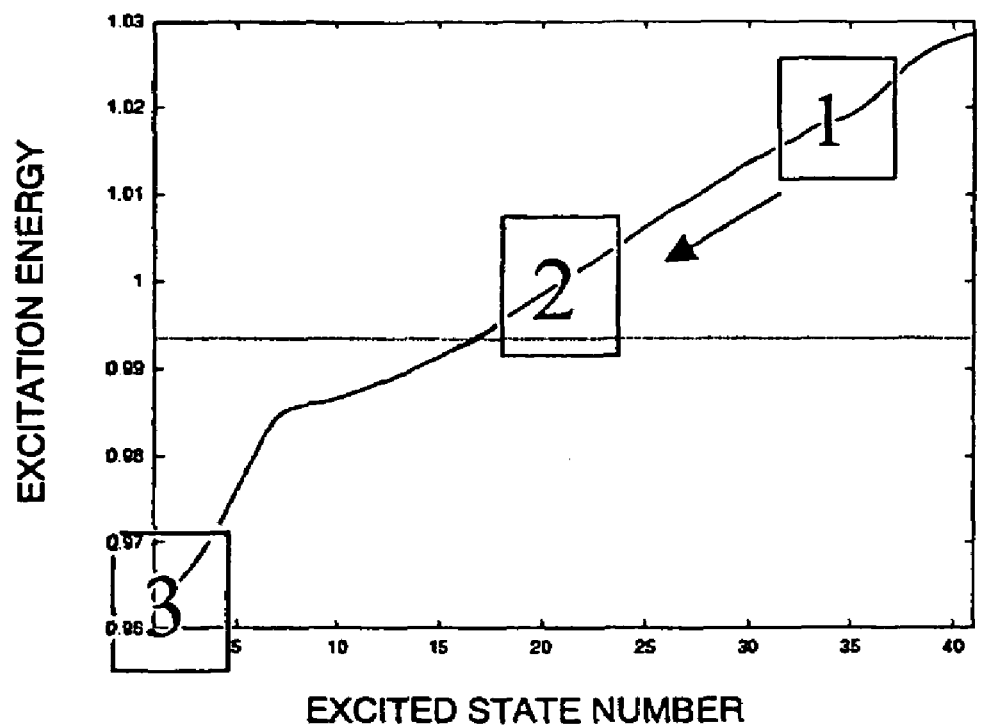
FIG. 13 is a schematic diagram showing a result of simulation carried out with the rectifier device according to the first embodiment of the invention.

Next explained is a result of simulation carried out with the rectifier device. The result is shown in FIGS. 12 and 13. FIG. 12 shows the aspect of transfer of the exciton 12 on linear molecules or molecule arrays 11 intersecting at a right angle, and x and y are coordinates of longer axes of each molecule or molecule array 11 when the branch is placed at the origin. FIG. 13 shows a relation between numbers of excited states and excitation energy.

It will be understood from FIGS. 12 and 13 that, when the polarization of the exciton 12 is the state of a high energy level (excitation energy) i.e., the state 1, the exciton 12 moves on the other molecule or molecule array 11 under the polarization that becomes a low energy level, i.e. the state 3, through the state of an intermediate energy level, i.e. the state 2.

Here is explained is a result of reviews on photo physical properties of a coordinate-bonded porphyrin array. As a preliminary study, first discussed is excitation energy (energy level) of a system of one-dimensional transition dipoles placed in parallel with each other, and it is reviewed that the sign of the excitation energy shift changes depending upon whether the direction of the system and the direction of each transition dipole is parallel or perpendicular. As already explained, this corresponds to the phenomenon that the energy level, i.e. the excitation energy, changes depending upon whether the exciton 12 is polarized perpendicularly or in parallel to the longer axis of the molecule or molecule array 11. Hereunder, based on these reviews, light absorption spectrums of coordinate-bonded porphyrin arrays will be calculated, and their properties will be discussed.

As to optical absorption of a system including a plurality of transition dipoles, a simple case is taken. Assume here an electron system in which sites are aligned in lattice interval a in a one-dimensional direction. Each site has two states, namely, ground state and excited state. Hereunder, only singlet excitation will be taken for consideration. Therefore, effects of spins do not apparently appear. Let the size of the system be sufficiently shorter than the wavelength of light having the energy required to bring about excitation at respective sites. In this case, variety in magnitude of the electric field of light depending upon the position inside the system is negligible. Interaction between electrons of the system and the electric field of light (denoted by E(t)) is given by the Hamiltonian of the following equation.

$$\hat{H}' = -\hat{d} \cdot E(t) \quad (1)$$

In the above equation, $\hat{d}$ is the transition dipole operator, and using the following position operator $\hat{r}$ the transition dipole operator is defined by the following equation.

$$\hat{d} = (-e)\hat{r} \quad (2)$$

In the above equation, (−e) is the electric charge of the electron. In general, transition dipole moment related to transition from the state |k> to |j> is give by the following equation.

$$d_{jk} = \langle j|\hat{d}|k\rangle \quad (3)$$

Magnitude of the interaction with the corresponding electric field of light is given by the following equation.

$$\langle j|\hat{H}'|k\rangle = d_{jk} \cdot E(t) \quad (4)$$

For simplicity, assume that all sites are equal in exciton energy (this excitation energy is denoted by $E_g$), but extension will be easy. Looking at only one excited state, the entire system has excited states equal in number to the number of sites (N). When the interaction between transition dipoles is negligible, their excitation energies are degenerate. When the transition dipole interaction is finite, the degeneracy is removed, and the respective excited states have various transition dipole moments. When the size of split of energies by the interaction is smaller than $E_g$, only these N excitation states have excitation energies near $E_g$. Hereunder, excitation states are discussed exclusively to them, but extension including two or more excited states will be easy.

The state of the entire system is expressed as follows.

$$|s_1, \ldots, s_j, \ldots, s_N\rangle = |s_1\rangle \ldots |s_j\rangle \ldots |s_N\rangle \quad (5)$$

In the above expression, $s_j$ is the state of site j, and expressed by $g_j$ when it is in the ground state, and by $e_j$ in the excited state. The ground state $|\Psi_0\rangle$ of the entire system is given by the following equation.

$$|\Psi_0\rangle = |g_1, \ldots, g_j, \ldots, g_N\rangle \quad (6)$$

The excited state of the entire system $|\Psi_v\rangle (v=1, \ldots, N)$ is linear combination of the excited states at individual sites, and it is expressed by $$|\Psi_v\rangle = \sum_{j=1}^{N} C_v^{(j)} |g_1, g_2, \ldots, g_{j-1}, e_j, g_{j+1}, \ldots, g_N\rangle \quad (7)$$

In the above equation, $|g_1, g_2, \ldots, g_{j-1}, e_j, g_{j+1}, \ldots, g_N\rangle$ is the excited state at the j-th site, and $C_v^{(j)}$ is a coefficient.

$|\Psi_v\rangle$ follows the Schrödinger equation below.

$$H|\Psi_v\rangle = E_v|\Psi_v\rangle \quad (8)$$

In the above equation, $E_v$ is the eigenenergy of $|\Psi_v\rangle$

Matrix elements of the Hamiltonian

H are blocked depending upon the ground state and the excited state, and are given as the following equation.

$$\langle g_1, \ldots, g_j, \ldots, g_N | H | g_1, \ldots, g_j, \ldots, g_N\rangle = 0$$

$$\langle g_1, \ldots, e_j, \ldots, g_N | H | g_1, \ldots, e_k, \ldots, g_N\rangle = \delta_{j,k} E_g = (1-\delta_{j,k}) V^{dd}(e_j, g_j; g_k, e_k) j, k=1, \ldots N \quad (9)$$

In the above equations, $V^{dd}(s_j, s_j'; s_k, s_k')$ is the interaction between transition dipoles $d_{s_j, s_j'}, d_{s_k, s_k'}$ that are positioned at sites i and j, respectively, and it is given by the following equation.

$$V^{dd}(s_j, s'_j; s_k, s'_k) = \frac{1}{4\pi\varepsilon|r_{ij}|^3}\left[d_{s_j,s'_j}\cdot d_{s_k,s'_k} - 3\frac{(d_{s_j,s'_j}\cdot r_{ij})(d_{s_k,s'_k}\cdot r_{ij})}{|r_{ij}|^2}\right] \quad (10)$$

In this equation, $\varepsilon$ is the dielectric constant. Further, $r_i$ and $r_j$ are coordinates of sites i and j, $r_{ij} = r_i - r_j$.

Magnitude of the transition dipole moment related to transition from the state $|\Psi_\nu\rangle$ to $|\Psi_\mu\rangle$ is generally given by the following equation.

$$d_{\mu\nu} = \langle\Psi_\mu|\hat{d}|\Psi_\nu\rangle \quad (11)$$

$$= \sum_{s_1=g_1}^{e_1}\sum_{s_2=g_2}^{e_2}\cdots\sum_{s_N=g_N}^{e_N}\sum_{s'_1=g_1}^{e_1}\sum_{s'_2=g_2}^{e_2}\cdots\sum_{s'_N=g_N}^{e_N}$$

$$\langle\Psi_\mu|s_1, s_2, \ldots, s_N\rangle d^{(N)}_{s_j,s'_j}\langle s'_1, s'_2, \ldots, s'_N|\Psi_\nu\rangle$$

In the above equation, $d^{(N)}_{s_j,s'_j}$ has been defined by the following equation.

$$d^{(N)}_{s_j,s'_j} = \delta_{s_1,s'_1}\cdots\delta_{s_{j-1},s'_{j-1}}d_{s_j,s'_j}\delta_{s_{j+1},s'_{j+1}}\cdots\delta_{s_N,s'_N} \quad (12)$$

As apparent from Equation (10), the interaction between the transition dipoles largely depends upon their placement, and this affects the excited state of the entire system and hence the optical response of the system. Hereunder, taking two different cases where transition dipoles of each site is parallel and perpendicular to the direction of the system (and lying on a common plane), transition dipole moments of excited states of respective cases and their light absorption are calculated.

In Case of Being Parallel

For convenience, the origin of coordinates are determined such that $r_j = (ja, 0, 0)$. Generality is not lost by this. Taken below is a simple situation in which transition dipoles are equal in all sites, and transition dipoles of site j are represented by $d_{ej,gj} = (d,0,0)$ In this case, transition dipole interaction appearing in Equation (9) is given from Equation (10) as follows.

$$V^{dd}(e_j,g_j;g_k,e_k) = -2V_d(j, k) \quad (13)$$

In this equation, $V_d(j, k)$ is given by $$V_d(j, k) = \frac{|d|^2}{4\pi\varepsilon|r_{jk}|^3} \quad (14)$$

When Equation (8) is solved under N=2, it is revealed that the system have the following two excited states.

$$|\Psi_1\rangle = \frac{1}{\sqrt{2}}(|e_1g_2\rangle + |g_1e_2\rangle), |\Psi_2\rangle = \frac{1}{\sqrt{2}}(|e_1g_2\rangle - |g_1e_2\rangle) \quad (15)$$

Their excitation energies are as follows.

$E_1 = E_g - 2V_d(1,2)$ $E_2 = E_g + 2V_d(1,2) \quad (16)$

Transition dipole moment between the states is calculated according to Equation (11). As an example, $d_{10}$ corresponding to transition from $|\Psi_0\rangle$ to $|\Psi_1\rangle$ is calculated as follows. $\quad (17)$ $$d_{10} = \langle\Psi_1|(|g_1g_2\rangle d_{g_1,e_1}\langle e_1g_2| + |g_1g_2\rangle d_{g_2,e_2}\langle g_1e_2| +$$
$$|e_1g_2\rangle d_{e_1,g_1}\langle g_1g_2| + |g_1e_2\rangle d_{e_2,g_2}\langle g_1g_2|)|\Psi_0\rangle$$

$$= \frac{1}{\sqrt{2}}(\langle e_1g_2| + \langle g_1e_2|)(d_{e_1,g_1}|g_1g_2\rangle +$$
$$d_{e_2,g_2}|g_2g_2\rangle)\langle g_1g_2|g_1g_2\rangle$$

$$= \frac{1}{\sqrt{2}}(d_{e_1,g_1} + d_{e_2,g_2})$$

$$= (\sqrt{2}d, 0, 0)$$

In substantially the same manner, the following is obtained.

$d_{00} = d_{11} = d_{22} = (0,0,0)$ $d_{01} = (d_{10})^* = (\sqrt{2}d^*,0,0)$ $d_{20} = d_{02} = (0,0,0)$ $d_{21} = d_{12} = (0,0,0) \quad (18)$ Therefore, excitation energy of an optically active state shifts to a lower energy side than $E_g$. Viscerally, when two transition dipoles parallel to the axis are aligned, Coulomb interaction energy is lower when charges having opposite signs are opposed than when charges with the same sign are opposed. Under the former placement, finite transition dipole moment remains; however, under the latter placement, transition dipole moments cancel each other and become zero.

In Case of Being Perpendicular

Here is reviewed a case in which transition dipoles are parallel and therefore lies on a common plane. In this case, without losing generality, $d_j = (0, d, 0)$ ($j=1, \ldots, N$) is employable. Transition dipole interaction of Equation (9) is given by the following equation.

$$V^{dd}(e_j,g_j;g_k,e_k) = +V_d(j, k) \quad (19)$$

In this equation, $V_d$ is the same as Equation (14). When N=2, the system has the excited state of Equation (15), and respective excitation energies and transition dipoles are as follows.

$$E_1 = E_g + V_d(r_1, r_2)$$

$$E_2 = E_g - V_d(r_1, r_2) \qquad (20)$$

$$d_{00} = d_{11} = d_{22} = (0,0,0)$$

$$d_{10} = (0, \sqrt{2}d, 0), \; d_{01} = (0, \sqrt{2}d^*, 0)$$

$$d_{20} = d_{02} = (0,0,0)$$

$$d_{21} = d_{12} = (0,0,0) \qquad (21)$$

Therefore, excitation energy of an optically active state shifts to a higher energy side than $E_g$. The higher energy state is more active optically. Similarly to the case of being parallel, this case can be viscerally understood. That is, since the repulsion between charges is smaller under the placement where transition dipoles align in opposite orientations and transition dipole moments cancel to zero, the energy is lower.

Optical Absorption

E is assigned to the electric field of incident light, and P is assigned to polarization induced thereby. Optical susceptibility ✦ is defined by the following equation.

$$P = \epsilon \chi E \qquad (22)$$

In case the electric field is not intensive, optical susceptibility ✦ can be described in the extent of linear responses. When the energy of the incident light is ω and the polarization direction is ▶(=x, y, z), ✦ is given by the following equation.

$$\chi(\omega) = \frac{1}{\varepsilon N} \sum_{v=1}^{N} \left[ \frac{|d_{v0}^\alpha|^2}{E_v - i\hbar\omega - i\hbar/\tau_v} + \frac{|d_{v0}^\alpha|^2}{E_v + i\hbar\omega + i\hbar/\tau_v} \right] \qquad (23)$$

In this equation, $$d_{v0}^\alpha, E_v$$

represent the ▶component and the excitation energy, respectively, of transition dipole moment from the ground state 0 to the excited state ▶, and $$\tau_v$$

represents the relaxation time of the excited state ▶. N is the total number of states. Light absorption is given by lm ✦ (ω).

Figure 14:
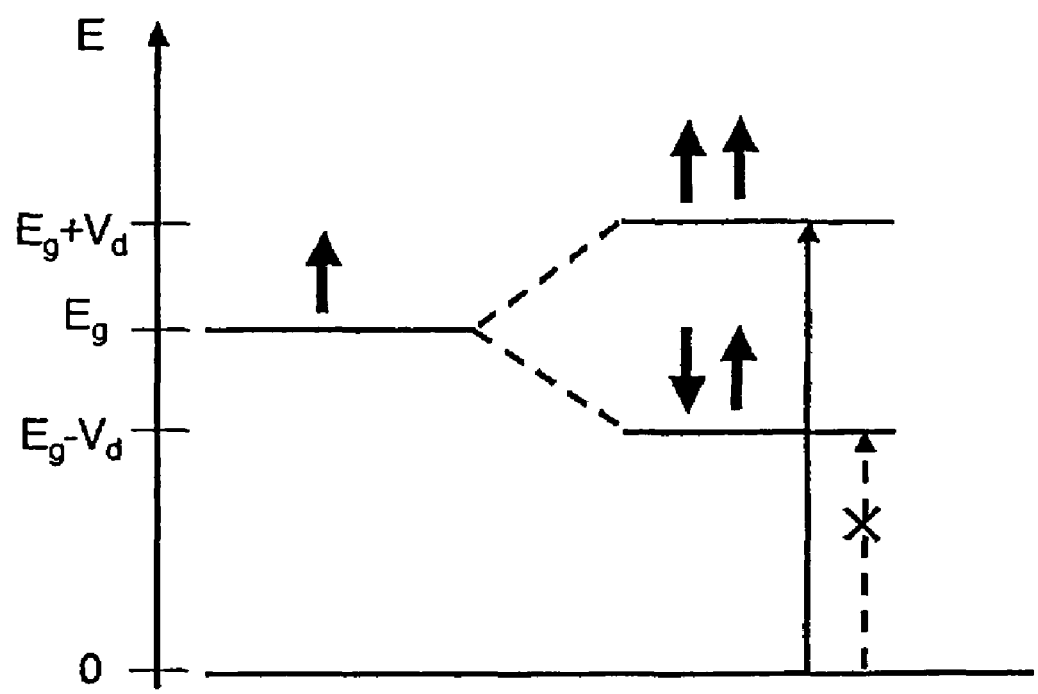
FIG. 14 is a schematic diagram showing an energy level diagram of a system having transition dipoles placed in parallel to the axis.
Figure 15:
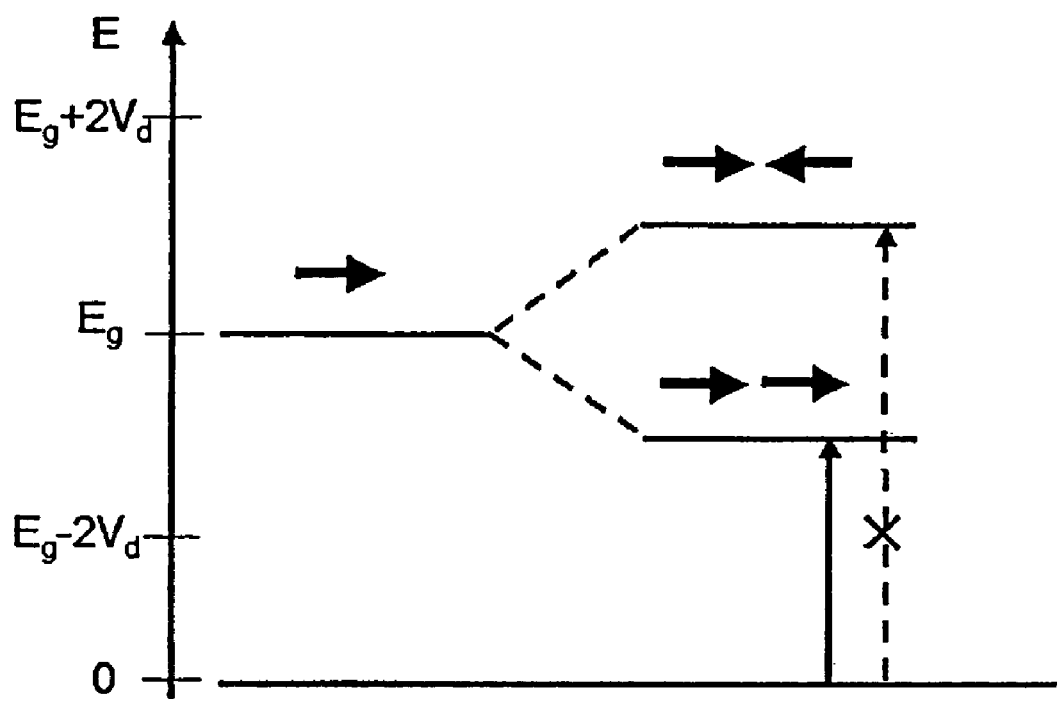
FIG. 15 is a schematic diagram showing an energy level diagram of a system having transition dipoles placed perpendicularly to the axis.

In general, in a system having transition dipoles placed in parallel to the axis, the energy of the optically active excited state shifts to the lower energy side (FIG. 14), and in a system having transition dipoles placed perpendicularly to the axis, the energy of the optically active excited state shifts to the higher energy side (FIG. 15).

As explained above, according to the first embodiment, the rectifier device of excitons based upon the novel operation principle heretofore unknown can be realized.

Next explained is the second embodiment of the invention.

In the second embodiment, an example building an ion sensor device by using the rectifier device according to the first embodiment will be explained.

Figure 16:
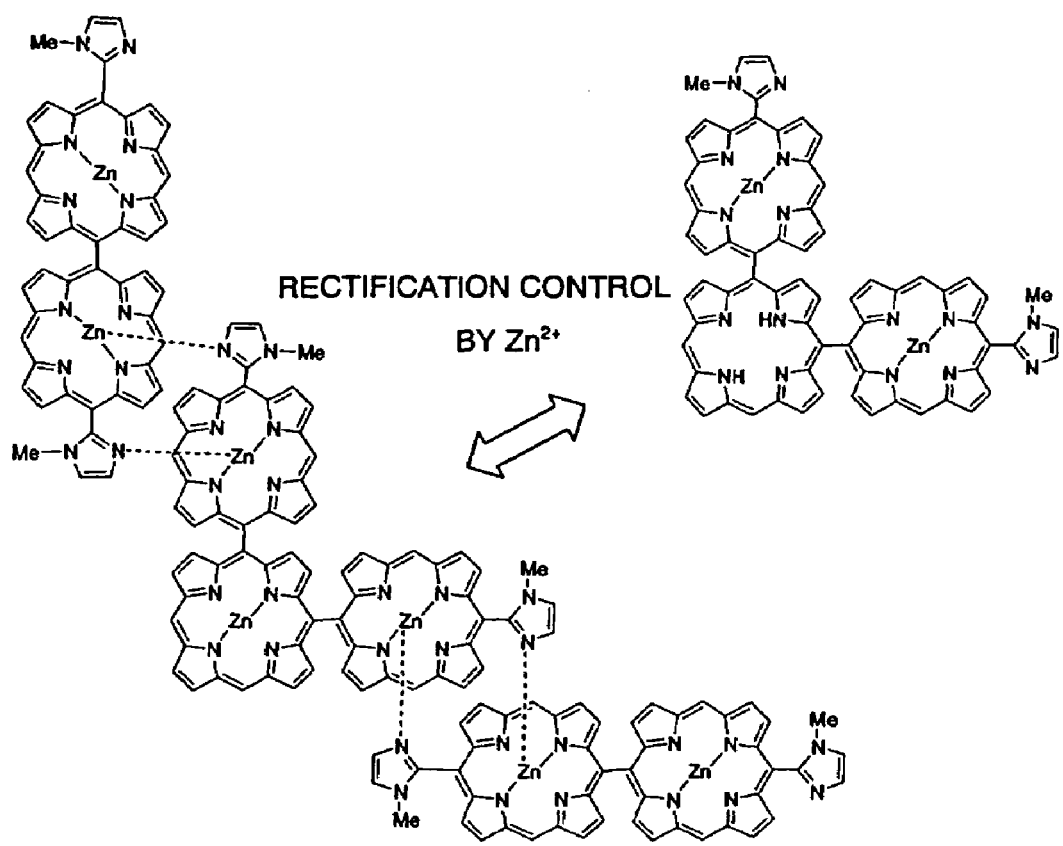
FIGS. 16A and 16B are schematic diagrams for explaining operations of an ion sensor device according to the second embodiment of the invention.

Although FIG. 16A is identical to FIG. 3B of the first embodiment, the effect of rectification of excitons changes depending upon whether or not the porphyrin ring at the center of the meso-coupled nonlinear imidazolyl porphyrin trimer corresponding to the junction site of the rectifier device has Zn as the central metal. That is, in the state shown in FIG. 16A, the porphyrin ring at the center of the meso-coupled nonlinear imidazolyl porphyrin trimer has Zn as central metal. However, if the porphyrin ring at the center of the meso-coupled nonlinear imidazolyl porphyrin trimer does not have Zn as the central metal as shown in FIG. 16B, then the rectifying effect of excitons is different between these two states. By using this principle, an ion sensor function can be realized.

In the other respects, the second embodiment is the same as the first embodiment, and explanation of the identical features is omitted here.

According to the second embodiment, the ion sensor device based upon the novel operation principle heretofore unknown can be realized.

Next explained is the third embodiment of the invention.

In the third embodiment, an example building a switching device by using the rectifier device according to the first embodiment will be explained.

The second embodiment was explained as realizing the ion sensor device by the use of changes in rectifying effect of excitons depending upon whether or not the porphyrin ring at the center of the meso-coupled nonlinear imidazolyl porphyrin trimer corresponding to the junction site of the rectifier device according to the first embodiment has Zn as the central metal. In the third embodiment, however, this principle is used to build a switching device capable of controlling rectification by ions. That is, in the state shown in FIG. 16A, the porphyrin ring at the center of the meso-coupled nonlinear imidazolyl porphyrin trimer has Zn as the central metal. However, if the porphyrin ring at the center of the meso-coupled nonlinear imidazolyl porphyrin trimer does not have Zn as the central metal as shown in FIG. 16B, then the rectifying effect of excitons is different between these two states. Therefore, by controlling $Zn^{2+}$ to enter in or exit from the porphyrin ring in the center, it is possible to control the effect of rectification by excitons and to thereby obtain a switching function.

In the other respects, the third embodiment is the same as the first embodiment, and explanation of the identical features is omitted here.

According to the third embodiment, the switching device based upon the novel operation principle heretofore unknown can be realized.

Figure 17:
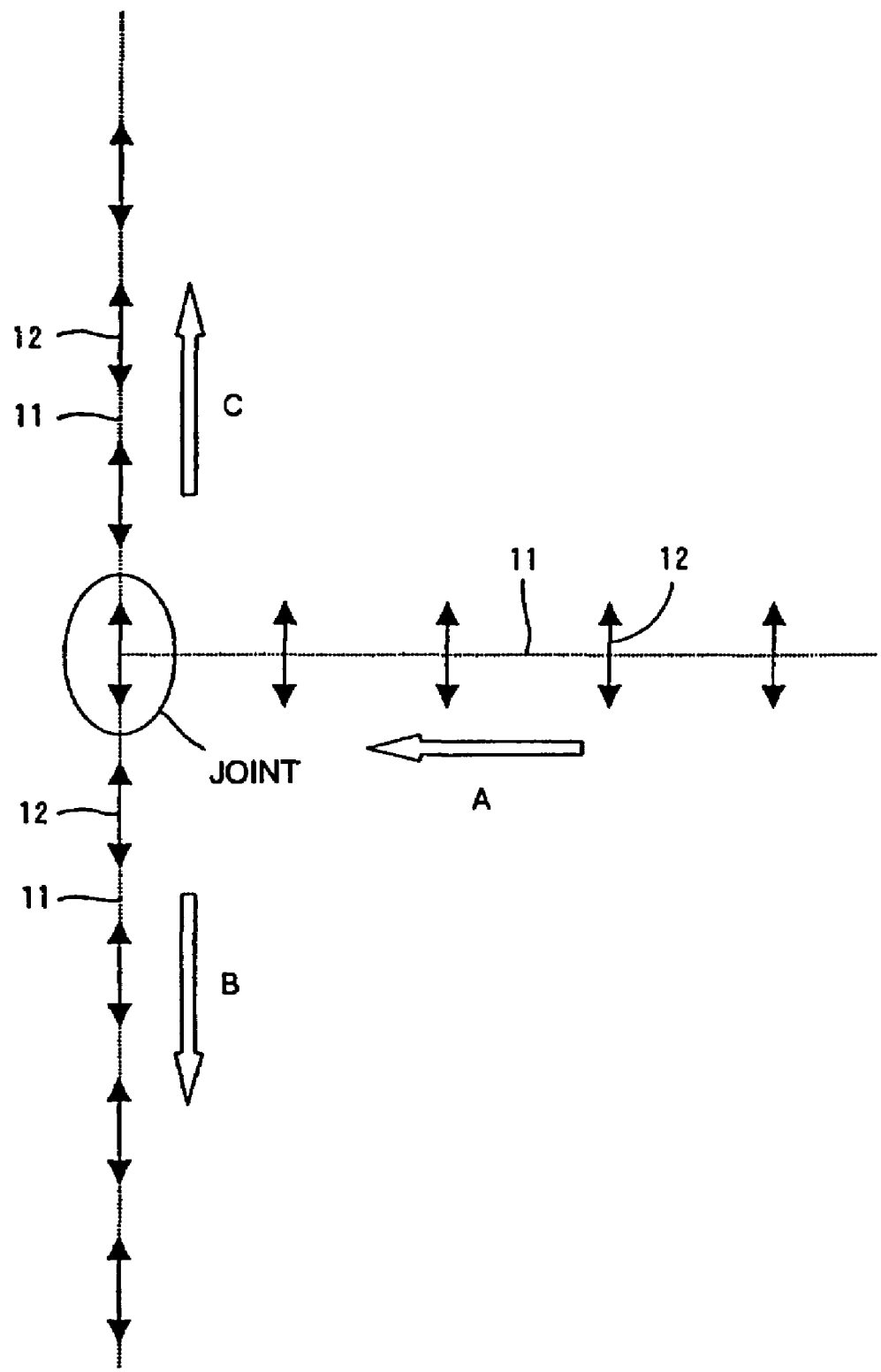
FIG. 17 is a schematic diagram showing a rectifier device according to the fourth embodiment of the invention.

FIG. 17 shows the fourth embodiment of the invention. Here is explained is a rectifying effect induced when three linear molecules or molecule arrays are coupled.

As shown in FIG. 17, in the fourth embodiment, a rectifier element is made by coupling three identical linear molecules or molecule arrays 11 into a T-shaped form as a whole.

In case that excitons 12 polarized perpendicularly to the longer axis of the molecule or molecule array 11 have a higher energy level than excitons 12 polarized in parallel, excitons 12 moving in the arrow A direction and entering into the joint separate as shown by arrows B and C with a higher probability. In this case, if excited states or excitons of the components of the molecules or molecule arrays 11 are equal in energy level between the arrow B and C directions, then the probabilities of excitons 12 to branch to the arrow B and C directions are equal. This is because, when the junction sites of the molecules or molecule arrays 11 extending in the arrow B and C directions among the three molecules or molecule arrays 11 are viewed from the molecule or molecule array 11 extending in the arrow A direction, joints at the junction sites have spatial symmetry.

Figure 18:
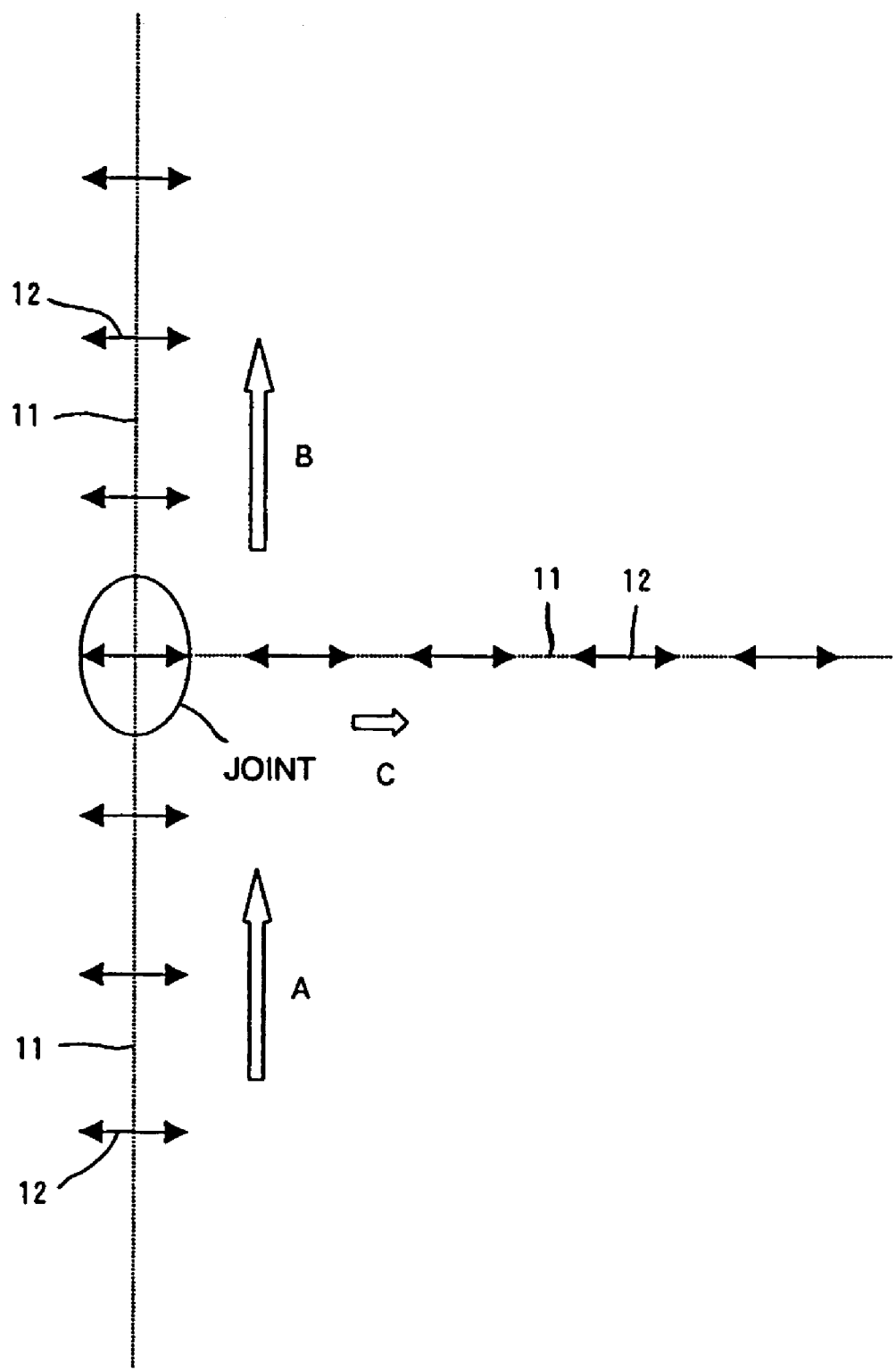
FIG. 18 is a schematic diagram showing a rectifier device according to the fourth embodiment of the invention.

In case of FIG. 18 where excitons 12 polarized perpendicularly to the longer axis of the molecule or molecule array 11 have a higher energy level than excitons 12 polarized in parallel, excitons 12 moving in the arrow A direction and entering into the joint separate as shown by arrows B and C with a higher probability. In this case, however, the probabilities of separating in the arrow B and C directions are not equal. This is because, when the junction sites of the molecules or molecule arrays 11 extending in the arrow B and C directions among the three molecules or molecule arrays 11 are viewed from the molecule or molecule array 11 extending in the arrow A direction, joints at the junction sites have spatial asymmetry.

Next explained is a concrete structure of the rectifier device.

Figure 19:
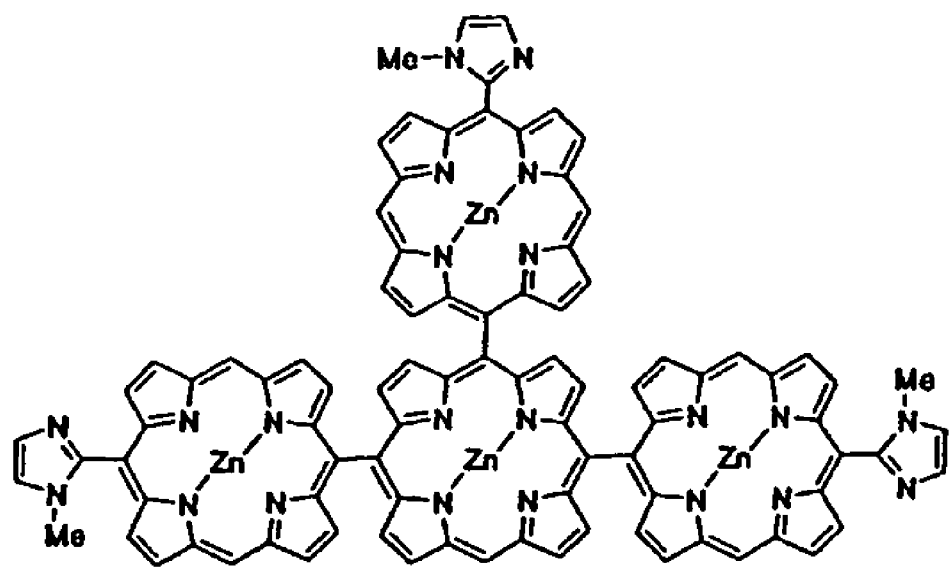
FIG. 19 is a schematic diagram for explaining a concrete structure of the rectifier device according to the fourth embodiment of the invention.

FIG. 19 shows a meso-coupled nonlinear imidazolyl porphyrin quadruple polymer. Using this meso-coupled nonlinear imidazolyl porphyrin quadruple polymer as the starting point, linear molecule arrays can be formed by coordinate bonding to extend in three directions in form of the letter T form as a whole, and the rectifier devices shown in FIGS. 17 and 18 can be made. Here again, as already explained in conjunction with the first embodiment, the building block forming the linear portion may be composed of either the meso-coupled linear imidazolyl porphyrin trimer shown in FIG. 3C or the meso-coupled linear imidazolyl porphyrin dimer of FIG. 2A.

In the other respects, the fourth embodiment is the same as the first embodiment, and explanation of the identical features is omitted here.

According to the fourth embodiment, the rectifier device based upon the novel operation principle heretofore unknown can be realized.

Next explained is the fifth embodiment of the invention.

In the fifth embodiment, an example building an ion sensor device by using the rectifier device according to the fourth embodiment will be explained.

The effect of rectification of excitons changes depending upon whether or not the porphyrin ring at the center of the meso-coupled nonlinear imidazolyl porphyrin quadruple polymer corresponding to the junction site of the rectifier device has Zn as the central metal. That is, in the state shown in FIG. 19, the porphyrin ring at the center of the meso-coupled nonlinear imidazolyl porphyrin quadruple polymer has Zn as the central metal. However, if the porphyrin ring at the center of the meso-coupled nonlinear imidazolyl porphyrin quadruple polymer does not have Zn as the central metal, then the rectifying effect of excitons is different between these two states. By using this principle, an ion sensor function can be realized.

In the other respects, the fifth embodiment is the same as the first embodiment, and explanation of the identical features is omitted here.

According to the fifth embodiment, the ion sensor device based upon the novel operation principle heretofore unknown can be realized.

Next explained is the sixth embodiment of the invention.

In the sixth embodiment, an example building a switching device by using the rectifier device according to the fourth embodiment will be explained.

The fifth embodiment was explained as realizing the ion sensor device by the use of changes in rectifying effect of excitons depending upon whether or not the porphyrin ring at the center of the meso-coupled nonlinear imidazolyl porphyrin quadruple polymer corresponding to the junction site of the rectifier device according to the fourth embodiment has Zn as the central metal. In the sixth embodiment, however, this principle is used to build a switching device capable of controlling rectification by ions. That is, in the state shown in FIG. 19, the porphyrin ring at the center of the meso-coupled nonlinear imidazolyl porphyrin quadruple polymer has Zn as the central metal. However, if the porphyrin ring at the center of the meso-coupled nonlinear imidazolyl porphyrin quadruple polymer does not have Zn as the central metal, then the rectifying effect of excitons is different between these two states. Therefore, by controlling $Zn^{2+}$ to enter in or exit from the porphyrin ring in the center, it is possible to control the effect of rectification by excitons and to thereby obtain a switching function.

In the other respects, the sixth embodiment is the same as the first embodiment, and explanation of the identical features is omitted here.

According to the sixth embodiment, the switching device based upon the novel operation principle heretofore unknown can be realized.

Figure 20:
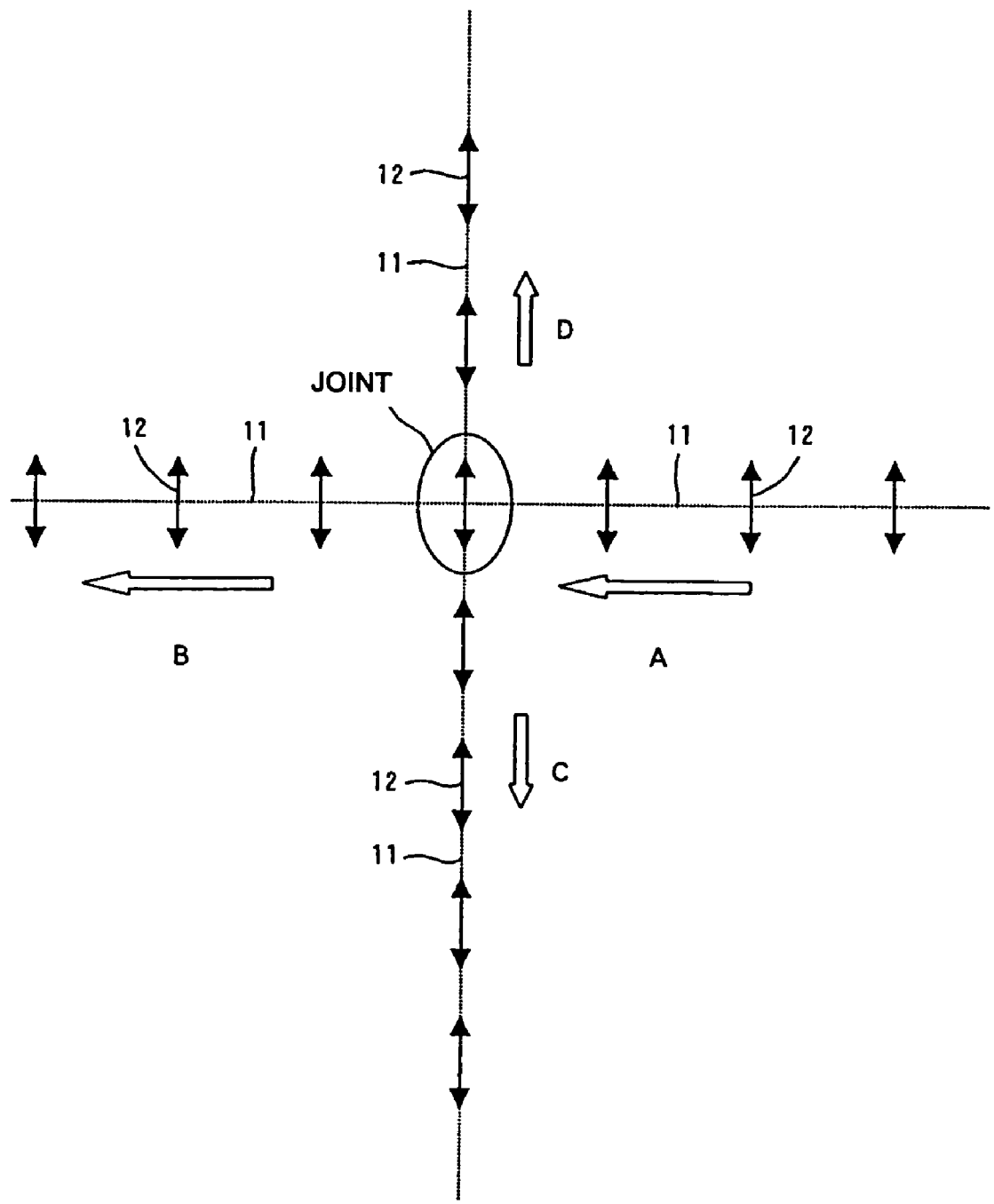
FIG. 20 is a schematic diagram showing a rectifier device according to the seventh embodiment of the invention.

FIG. 20 shows the seventh embodiment of the invention. Here is explained is a rectifying effect induced when four linear molecules or molecule arrays are coupled at a right angle.

As shown in FIG. 20, in the seventh embodiment, a rectifier element is made by coupling four identical linear molecules or molecule arrays 11 into a cross-shaped form as a whole.

In case that excitons 12 polarized perpendicularly to the longer axis of the molecule or molecule array 11 have a higher energy level than excitons 12 polarized in parallel, excitons 12 moving in the arrow A direction and entering into the joint separate as shown by arrows B, C and D with a higher probability. In this case, if the arrow C and arrow D directions are symmetrical in energy, then the probabilities of excitons 12 to separate in the arrow C and arrow D directions are equal with a higher probability, and the probabilities of excitons 12 to separate in the arrow B is not equal to them.

Next explained is a concrete structure of the rectifier device.

Figure 21:
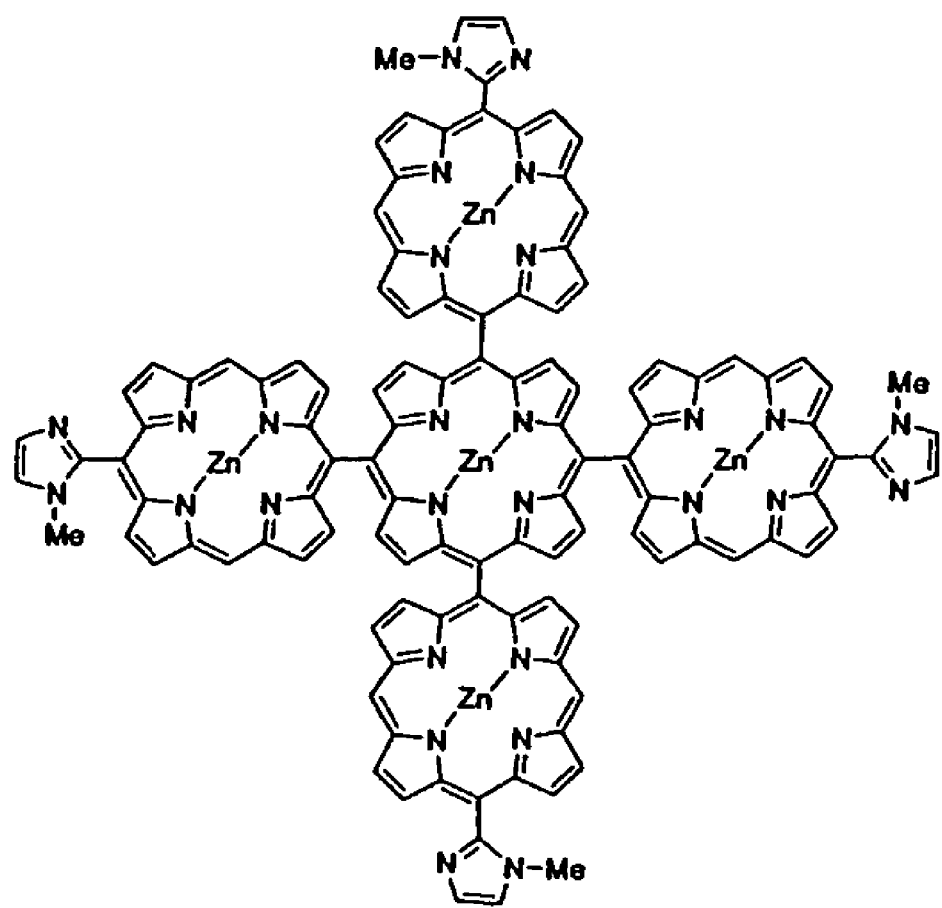
FIG. 21 is a schematic diagram for explaining a concrete structure of the rectifier device according to the seventh embodiment of the invention.

FIG. 21 shows a meso-coupled nonlinear imidazolyl porphyrin quintuple polymer. Using this meso-coupled nonlinear imidazolyl porphyrin quintuple polymer as the starting point, a linear molecule arrays can be formed by coordinate bonding to extend in four directions in a cross-shaped form as a whole, and the rectifier device shown in FIG. 20 can be made. Here again, as already explained in conjunction with the first embodiment, the building block forming the linear portion may be composed of either the meso-coupled linear imidazolyl porphyrin trimer shown in FIG. 3C or the meso-coupled linear imidazolyl porphyrin dimer of FIG. 2A.

In the other respects, the seventh embodiment is the same as the first embodiment, and explanation of the identical features is omitted here.

According to the seventh embodiment, the rectifier device based upon the novel operation principle heretofore unknown can be realized.

Next explained is the eighth embodiment of the invention.

In the eighth embodiment, an example building an ion sensor device by using the rectifier device according to the seventh embodiment will be explained.

The effect of rectification of excitons changes depending upon whether or not the porphyrin ring at the center of the meso-coupled nonlinear imidazolyl porphyrin quintuple polymer corresponding to the junction site of the rectifier device has Zn as the central metal. That is, in the state shown in FIG. 21, the porphyrin ring at the center of the meso-coupled nonlinear imidazolyl porphyrin quintuple polymer has Zn as the central metal. However, if the porphyrin ring at the center of the meso-coupled nonlinear imidazolyl porphyrin quintuple polymer does not have Zn as the central metal, then the rectifying effect of excitons is different between these two states. By using this principle, an ion sensor function can be realized.

In the other respects, the eighth embodiment is the same as the first embodiment, and explanation of the identical features is omitted here.

According to the eighth embodiment, the ion sensor device based upon the novel operation principle heretofore unknown can be realized.

Next explained is the ninth embodiment of the invention.

In the ninth embodiment, an example building a switching device by using the rectifier device according to the seventh embodiment will be explained.

The eighth embodiment was explained as realizing the ion sensor device by the use of changes in rectifying effect of excitons depending upon whether or not the porphyrin ring at the center of the meso-coupled nonlinear imidazolyl porphyrin quintuple polymer corresponding to the junction site of the rectifier device according to the seventh embodiment has Zn as the central metal. In the ninth embodiment, however, this principle is used to build a switching device capable of controlling rectification by ions. That is, in the state shown in FIG. 21, the porphyrin ring at the center of the meso-coupled nonlinear imidazolyl porphyrin quintuple polymer has Zn as the central metal. However, if the porphyrin ring at the center of the meso-coupled nonlinear imidazolyl porphyrin quintuple polymer does not have Zn as the central metal, then the rectifying effect of excitons is different between these two states. Therefore, by controlling $Zn^{2+}$ to enter in or exit from the porphyrin ring in the center, it is possible to control the effect of rectification by excitons and to thereby obtain a switching function.

In the other respects, the ninth embodiment is the same as the first embodiment, and explanation of the identical features is omitted here.

According to the ninth embodiment, the switching device based upon the novel operation principle heretofore unknown can be realized.

Next explained is the tenth embodiment of the invention.

In the tenth embodiment, an example is explained which inserts a resistor device between the molecules or molecule arrays composing the rectifier device in the first to ninth embodiment.

Figure 22A:
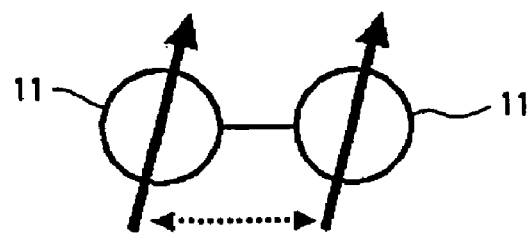
FIGS. 22A and 22B are schematic diagrams showing a rectifier device according to the tenth embodiment of the invention.
Figure 22B:
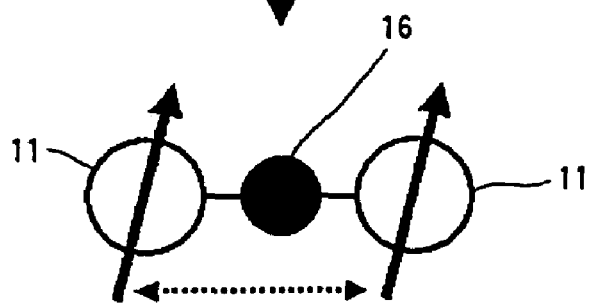

That is, in the tenth embodiment, instead of directly coupling adjacent molecules or molecule arrays 11 as shown in FIG. 22A, adjacent molecules or molecule arrays 11 are coupled indirectly via a resistor device 16 as shown in FIG. 22B to statically change (in this case, increase) the distance between the molecules or molecule arrays 11 at opposite ends of the resistor device 16. In FIGS. 22A and 22B, arrows on the molecules or molecule arrays 11 show transition dipole moments (also in FIGS. 24A and 24B explained later). Used as the resistor device 16 is another molecule or molecule array, especially an organic molecule or an organic molecule array, which is capable of covalent bonding with the molecules or molecule arrays 11 at the opposite ends.

Amplitude of transition dipole moment near the resistor device 16 in the exciton state changes with a change of the distance between the molecules or molecule arrays 11 at opposite ends of the resistor device 16, and it functions as a resistor against excitation transfer. Additionally, since the transition dipole moment of the entire exciton state also changes, the number of excitable exciton states varies upon irradiation of an electromagnetic wave (such as light, especially visible light).

Figure 23:
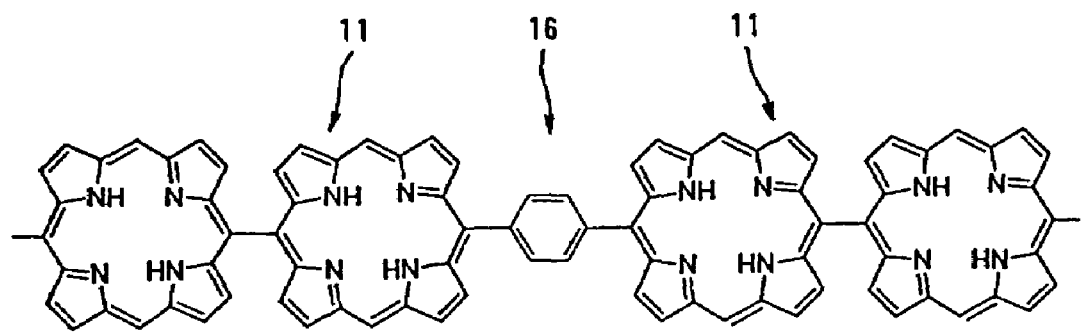
FIG. 23 is a schematic diagram for explaining a concrete structure of the rectifier device according to the tenth embodiment of the invention.

FIG. 23 shows a concrete structure of a rectifier device with the resistor device 16 inserted therein. In this example, porphyrin molecules are used as the molecules or molecule arrays 11 building the rectifier device, and benzene is used as the resistor device 16.

When the rectifier device is formed by coupling a plurality of identical molecules or molecule arrays 11, for example, such as organic molecules, their coupling distance is constant. In the tenth embodiment, however, since the resistor device 16 is inserted in the rectifier device, the distance between the molecules or molecule arrays 11 at opposite ends of the resistor device 16 can be changed, and this makes it possible to form the exciton state and hence control the excitation transfer.

Next explained is the eleventh embodiment of the invention.

Here again, similarly to the tenth embodiment, an example inserting a resistor device between molecules or molecule arrays building the rectifier device will be explained.

Figure 24A:
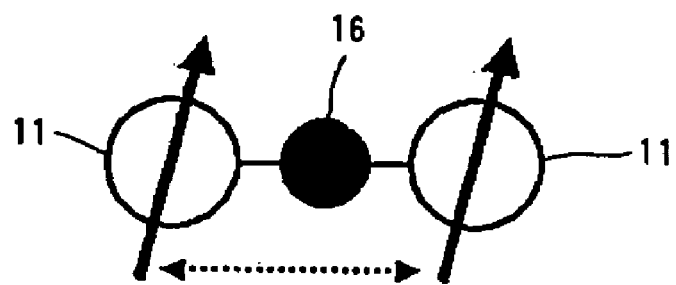
FIGS. 24A and 24B are schematic diagrams showing a rectifier device according to the eleventh embodiment of the invention.
Figure 24B:
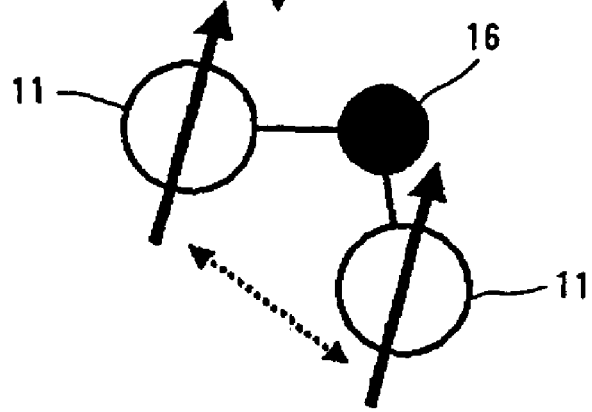

That is, in the eleventh embodiment, adjacent molecules or molecule arrays 11 are connected by a resistor device 16 inserted therein as shown in FIG. 24A. In this case, used as the resistor device 16 is another molecule or molecule array, especially an organic molecule or an organic molecule array, which can couple with the molecules or molecule arrays 11 at the opposite ends by covalent bonding and varies in three-dimensional structure upon irradiation of an electromagnetic wave such as light. Thus, when an electromagnetic wave is applied, the rectifier device is bent from the condition shown in FIG. 24A, in which the molecules or molecule arrays 11 and the resistor device 16 align straight, to the condition shown in FIG. 24B, in which the coupling direction between the molecule or molecule array 11 coupling with one end of the resistor device 16 is bent from the coupling direction of the molecule or molecule array 11 coupling with the other end of the resistor device 16. Therefore, distance between the molecules or molecule arrays 11 at opposite ends of the resistor device 16 dynamically changes (in this case, increases).

In response to a change of the distance between the molecules or molecule arrays 11 at opposite ends of the resistor device 16, transition dipole moment near the resistor device 16 in the exciton state varies in amplitude, and functions as a resistor against excitation transfer. Additionally, since the transition dipole moment of the entire exciton state also changes, the number of excitable exciton states varies upon irradiation of an electromagnetic wave.

Figure 25:
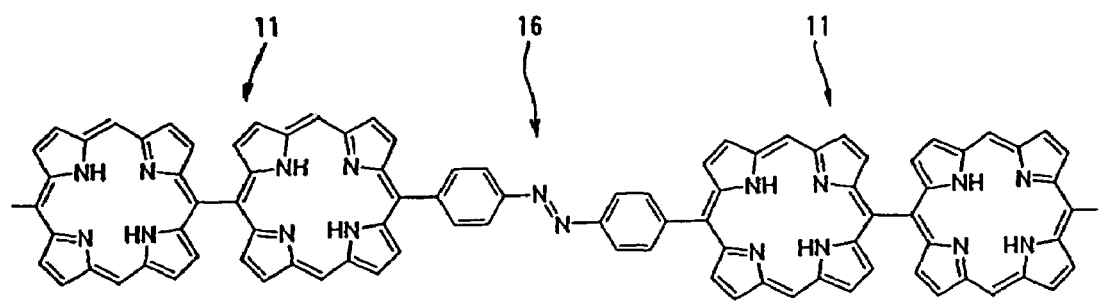
FIG. 25 is a schematic diagram for explaining a concrete structure of the rectifier device according to the eleventh embodiment of the invention.

FIG. 25 shows a concrete example of a structure of the rectifier device having the resistor device 16 inserted therein. In this example, porphyrin molecules are used as the molecules or molecule arrays 11 building the rectifier device, and azobenzene having cis- and trans-type stereoisomers is used as the resistor device 16. In this case, ultraviolet light can be used as an electro-magnetic wave irradiated to cause transition from the state shown in FIG. 24A to the state shown in FIG. 24B and inverse transition can be performed by irradiation of visible light or thermally. When molecules having bonds capable of causing cis-trans transition such as benzene are used, means of changing conjugation length by values of pH such as certain indicators (Methyl Orange, Methy Yellow, Methyl Red, or the like) may be used.

When the rectifier device is formed by coupling a plurality of identical molecules or molecule arrays 11, for example, such as organic molecules, their coupling distance is constant. In the eleventh embodiment, however, since the resistor device 16 is inserted in the rectifier device such that the distance between the molecules or molecule arrays 11 at opposite ends of the resistor device 16 can be changed by inviting a change in structure by irradiation of an electromagnetic wave, it is possible to form the exciton state and hence control the excitation transfer.

Having described specific preferred embodiments of the present invention with reference to the accompanying drawings, it is to be understood that the invention is not limited to those precise embodiments, and that various changes and modifications may be effected therein by one skilled in the art without departing from the scope or the spirit of the invention as defined in the appended claims.

For example, numerical values, structures, substances, source materials, reaction, and so on, were shown only for examples, and other numerical values, structures, substances, source materials, reaction, and so on, may be used where necessary.

According to the invention, a molecular device, molecule array, rectifier device, rectifying method, sensor device, switching device, circuit device, logical circuit device and information processing device based on the novel principle of operation can be realized.

What is claimed is:

1. A molecular device comprising at least two molecules or molecule arrays and including a rectifying function to cause asymmetrical progress of transfer of an excited state or exciton, wherein each of the at least two molecules or molecule arrays has a straighter linear shape, and can be excited directly by light or can make an excited state by transfer of excitation energy from an adjacent one of the molecules or molecule arrays, wherein at least one of the at least two molecules or molecule arrays is one of:

a conjugate polymer in form of a linear chain, a non-conjugate polymer in form of a linear chain, or a linear molecule aggregate composed of the same or different kinds of molecules, and wherein the at least two molecules or molecule arrays form substantially a right angle at terminal ends of the molecules or molecule arrays.

* * * * *